US011414687B2

(12) United States Patent
Hoff et al.

(10) Patent No.: US 11,414,687 B2
(45) Date of Patent: Aug. 16, 2022

(54) METHOD AND SYSTEM FOR ENZYMATIC SYNTHESIS OF OLIGONUCLEOTIDES

(71) Applicant: CENTRILLION TECHNOLOGY HOLDINGS CORPORATION, Grand Cayman (KY)

(72) Inventors: Kendall Hoff, San Francisco, CA (US); Michelle Halpain, Stanford, CA (US); Giancarlo Garbagnati, Redwood City, CA (US); Wei Zhou, Saratoga, CA (US)

(73) Assignee: Centrillion Technology Holdings Corporation, Grand Cayman (KY)

( * ) Notice: Subject to any disclaimer, the term of this patent is extended or adjusted under 35 U.S.C. 154(b) by 134 days.

(21) Appl. No.: 16/651,544

(22) PCT Filed: Oct. 1, 2018

(86) PCT No.: PCT/US2018/053776
§ 371 (c)(1),
(2) Date: Mar. 27, 2020

(87) PCT Pub. No.: WO2019/070593
PCT Pub. Date: Apr. 11, 2019

(65) Prior Publication Data
US 2020/0263218 A1 Aug. 20, 2020

Related U.S. Application Data

(60) Provisional application No. 62/727,174, filed on Sep. 5, 2018, provisional application No. 62/568,205, filed on Oct. 4, 2017.

(51) Int. Cl.
*C12Q 1/68* (2018.01)
*C12P 19/34* (2006.01)
*C12N 9/12* (2006.01)

(52) U.S. Cl.
CPC ............ *C12P 19/34* (2013.01); *C12N 9/1252* (2013.01); *C12Y 207/07007* (2013.01)

(58) Field of Classification Search
CPC ........................................................ C12Q 1/68
(Continued)

(56) References Cited

U.S. PATENT DOCUMENTS

| 5,518,900 A * | 5/1996 | Nikiforov | ............ C12Q 1/6858 |
| | | | 536/23.1 |
| 6,245,507 B1 * | 6/2001 | Bogdanov | .......... G01N 21/6428 |
| | | | 204/461 |

(Continued)

OTHER PUBLICATIONS

International Search Report and Written Opinion for corresponding PCT Application No. PCT/US2018/053776, dated Jan. 8, 2019.
(Continued)

*Primary Examiner* — Aaron A Priest
(74) *Attorney, Agent, or Firm* — Wilson Sonsini Goodrich & Rosati

(57) ABSTRACT

The present disclosure relates to methods, processes and systems for enzymatic synthesis of oligonucleotide from a single-stranded, immobilized primer in the presence of a polymerase. Using the disclosed methods single-stranded oligonucleotides can be synthesized enzymatically from a single-stranded, immobilized primer in the presence of deoxyribonucleotide triphosphates or ribonucleotide triphosphates. Dideoxyribonucleotide triphosphates, deoxyribonucleotide triphosphates with reversible terminators, or ribonucleotide triphosphates with reversible terminators can be added enzymatically to the end of the primer or its extension products. According to the disclosed method, a single-stranded primer can bind to a template such that the thus-formed double-stranded structure can allow the polymerase to extend the primer at 3' end.

14 Claims, 11 Drawing Sheets

Specification includes a Sequence Listing.

(58) Field of Classification Search
USPC .......................................................... 435/6.1
See application file for complete search history.

(56) References Cited

U.S. PATENT DOCUMENTS

| | | | | |
|---|---|---|---|---|
| 6,294,336 | B1* | 9/2001 | Boyce-Jacino | ...... C12Q 1/6874 |
| | | | | 435/6.12 |
| 6,824,980 | B2* | 11/2004 | Wang | ................... C12Q 1/6851 |
| | | | | 435/7.1 |
| 7,858,311 | B2* | 12/2010 | Williams | ............. C12Q 1/6869 |
| | | | | 435/6.12 |
| 9,017,973 | B2* | 4/2015 | Gordon | ................ C12Q 1/6869 |
| | | | | 536/26.6 |
| 9,624,539 | B2* | 4/2017 | Ju | ........................... C07H 19/06 |
| 10,844,430 | B2* | 11/2020 | Andruzzi | ............. C12Q 1/6806 |
| 2002/0090618 | A1 | 7/2002 | Smith et al. | |
| 2005/0019793 | A1 | 1/2005 | Kurn et al. | |
| 2005/0202490 | A1 | 9/2005 | Makarov et al. | |
| 2005/0260609 | A1* | 11/2005 | Lapidus | ............... C12Q 1/6869 |
| | | | | 536/24.3 |
| 2006/0141503 | A1* | 6/2006 | Wang | ................... C12Q 1/6858 |
| | | | | 435/6.12 |
| 2010/0167938 | A1* | 7/2010 | Su | ........................ C12Q 1/6874 |
| | | | | 506/7 |
| 2012/0157322 | A1 | 6/2012 | Myllykangas et al. | |
| 2014/0242579 | A1 | 8/2014 | Zhou et al. | |
| 2015/0329855 | A1 | 11/2015 | Gray et al. | |
| 2016/0257984 | A1* | 9/2016 | Hardenbol | ........... C12Q 1/6806 |
| 2016/0355541 | A1* | 12/2016 | Jain | ..................... C12Q 1/6869 |
| 2017/0044524 | A1 | 2/2017 | Pollom, Jr. et al. | |
| 2017/0067095 | A1 | 3/2017 | McGall et al. | |

OTHER PUBLICATIONS

Turcatti, et al., "A New Class of Cleavable Fluorescent Nucleotides: Synthesis and Optimization as Reversible Terminators for DNA sequencing by Synthesis," Nucleic Acids Research, Feb. 7, 2008, vol. 36, No. 4, e25, pp. 1-13.

* cited by examiner

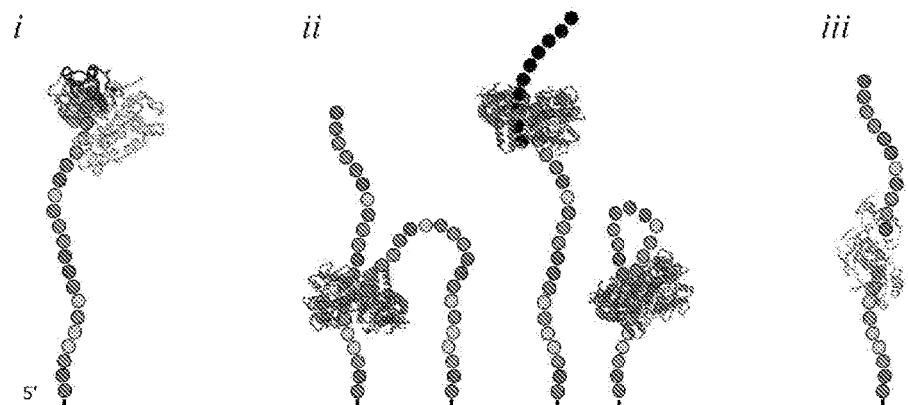
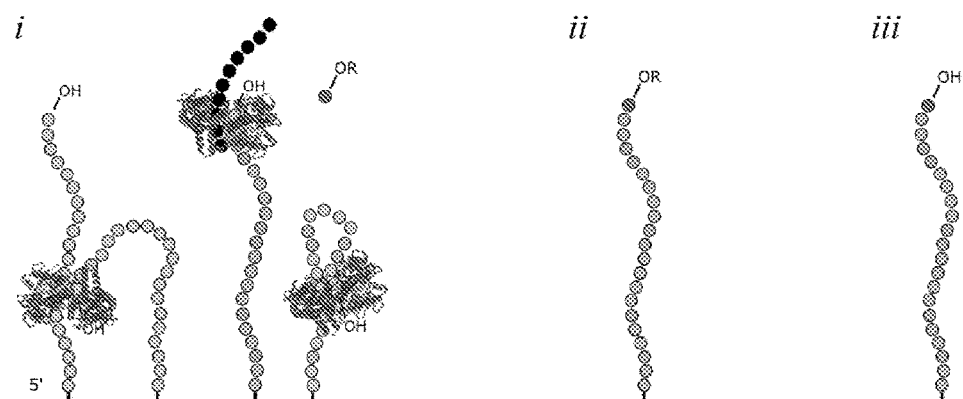
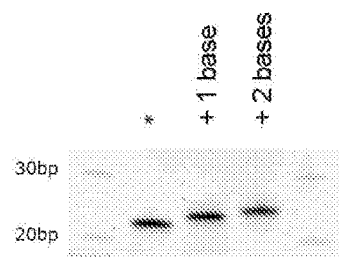
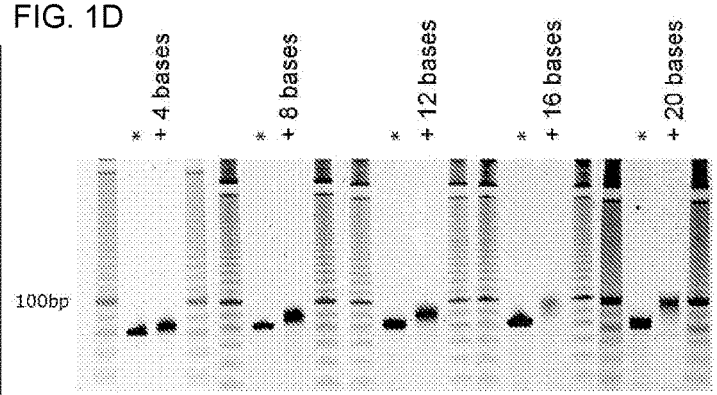

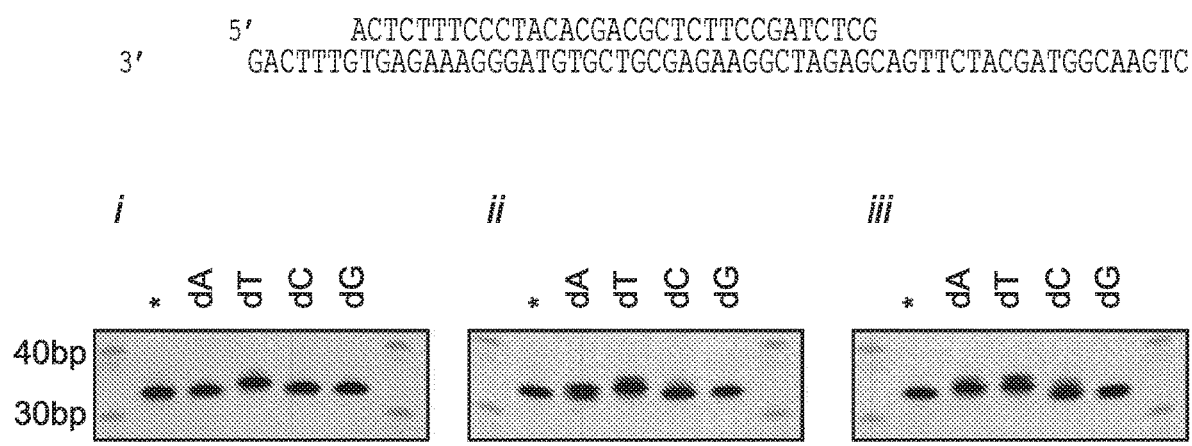
FIG. 4A
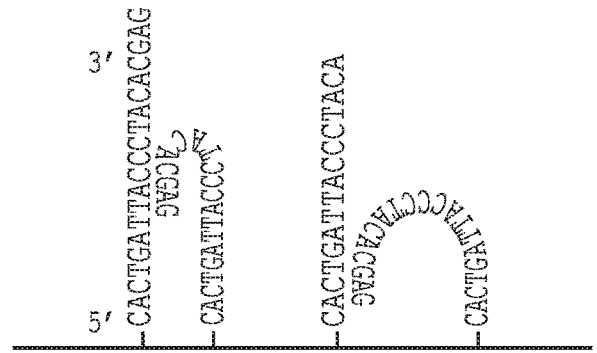
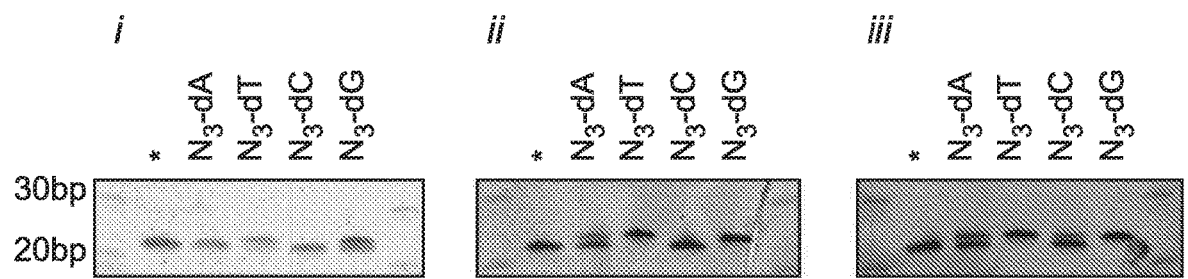
FIG. 4B

| Oligonucleotide Name | Sequence 5' - 3' | Use |
|---|---|---|
| UTO-1 | /5Biosg/TTTTTACCTCTGTATGCATCGATAGGTCCGGGAAGCCCACAAACTAATTTCAGAGTGACGTTACTTGGGCCTTTTTTT/3deoxyU/ | Single-stranded DNA Extension |
| ESO-1 | TACGATTCAGCTGATACAGC | Synthesized with Duplase-3 |
| UTO-1p | CAAACTAATTTCAGAGTGACGTTACTTGGGCCTTTTTTT | Sequencing analysis |
| UTO-1p2 | ACGTTACTTGGCGC | Sequencing analysis |
| SPO-1 | /5Biosg/CACTGATTAGCCTACACGAG | Single-stranded DNA Extension |
| SPO-2 | /5Biosg/GTGACTAATGGGATGTCCTC | Single-stranded DNA Extension |
| SPO-3 | /5Biosg/CACTGATTCTCTACACGAG | Single-stranded DNA Extension |
| SPO-4 | /5Biosg/CACTGATTAGGCTACACGAG/ | Single-stranded DNA Extension |
| SPO-30bp | /5Biosg/CTGAACGCTAGCATCTTGACGAGATCGGAAGAGCGTCGTGTAGGGAAAGAGTGTTTCAG | Single-stranded DNA Extension |
| T18-Biot | /5Biosg/TTTTTTTTTTTTTTTTTT | Single-stranded DNA Extension |
| T20-Biot | /5Biosg/TTTTTTTTTTTTTTTTTTTT | Single-stranded DNA Extension |
| T7CAAT20-Biot | /5Biosg/TTTTTTCAATTTTTTTTTTTTTTTTTTTT | Single-stranded DNA Extension |
| A6-P | AAAAAA/3Phos/ | In-solution Templates |
| CA5-P | CAAAAA/3Phos/ | In-solution Templates |
| C2A5-P | CCAAAA/3Phos/ | In-solution Templates |
| C3A3-P | CCCAAA/3Phos/ | In-solution Templates |
| C4A2-P | CCCCAA/3Phos/ | In-solution Templates |
| C5-A-P | CCCCCA/3Phos/ | In-solution Templates |
| C6-P | CCCCCC/3Phos/ | In-solution Templates |
| N6-P | NNNNNN/3Phos/ | In-solution Templates |
| N9-P | NNNNNNNNN/3Phos/ | In-solution Templates |
| N12-P | NNNNNNNNNNNN/3Phos/ | In-solution Templates |
| N15-P | NNNNNNNNNNNNNNN/3Phos/ | In-solution Templates |
| N18-P | NNNNNNNNNNNNNNNNNN/3Phos/ | In-solution Templates |
| N21-P | NNNNNNNNNNNNNNNNNNNNN/3Phos/ | In-solution Templates |

FIG. 10

| | | |
|---|---|---|
| NS-P | NNNN/3Phos/ | In-solution Templates |
| CTCGT-P | CTCGT/3Phos/ | In-solution Templates |
| CN4-P | CNNNN/3Phos/ | In-solution Templates |
| TCTCG-P | TCTCG/3Phos/ | In-solution Templates |
| TN5-P | TNNNNN/3Phos/ | In-solution Templates |
| TCN3-P | TCNNN/3Phos/ | In-solution Templates |
| ds-template | 5Bioag/CTGAACGGTAGCATCTTGACGAGATCGGAAGAGCGTCGTGTAGGGAAAGAGTGTTTCAG | Primer Extension |
| ds-primer1 | ACTCTTTCCCTACACGACGCTCTTCCGATCTCG | Primer Extension |
| ds-primer2 | CACTCTTTCCCTACACGACGCTCTTCCGATCTC | Primer Extension |
| PCR-ESO1-F | TATGCATCTACACTCTTTCCCTACACGACGCTCTTCCGATCTTTTTTTTTACCTCT*G | Sequencing Library Preparation |
| P7-Poly(T) | CTCGGCATTCCTGCTGAACCGCTCTTCCGATCTTTTTTTTTTTTTTTTTTTT*T | Sequencing Library Preparation |

FIG. 10 (Cont.)

SEQUENCE LISTING

```
<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gctgtatcgg ctgaatcgta                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cactgattac cctacacgag                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cactgaattc cctacacgag                                                    20

<210> SEQ ID NO 4
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tttttacctc tgtatgcatc gataggtccg ggaagcccac aaactaattt cagagtgacg        60
ttacttggcg cttttttt                                                      77

<210> SEQ ID NO 5
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 5
tttttttttt tttttttttt                                              20

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 ttttttttcaa tttttttttt tttttttttt                                  30

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cactctttcc ctacacgacg ctcttccgat ctc                               33

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctgaacggta gcatcttgac gagatcggaa gagcgtcgtg tagggaaaga gtgtttcag   59

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtgactaatg ggatgtgctc                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cactgatttc tctacacgag                                              20

<210> SEQ ID NO 11
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 11
cactgattag gctacacgag                                                    20

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
actctttccc tacacgacgc tcttccgatc tcg                                     33

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cactgattac cctaca                                                        16

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tttttttttt tttttttt                                                      18

<210> SEQ ID NO 15
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
tttttacctc tgtatgcatc gataggtccg ggaagcccac aaactaattt cagagtgacg        60
ttacttggcg cttttttu                                                      78

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tacgattcag ccgatacagc                                                    20

<210> SEQ ID NO 17
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caaactaatt tcagagtgac gttacttggc gctttttt                               39

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
acgttacttg gcgc                                                        14

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cactgattac cctacacgag                                                  20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtgactaatg ggatgtgctc                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cactgatttc tctacacgag                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cactgattag gctacacgag                                                  20

<210> SEQ ID NO 23
<211> LENGTH: 59
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ctgaacggta gcatcttgac gagatcggaa gagcgtcgtg tagggaaaga gtgtttcag       59

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tttttttttt tttttttt                                                    18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tttttttttt tttttttttt                                                  20

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tttttttcaa tttttttttt tttttttttt                                       30

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
actctttccc tacacgacgc tcttccgatc tcg                                   33

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cactctttcc ctacacgacg ctcttccgat ctc                                   33

<210> SEQ ID NO 29
<211> LENGTH: 54
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 29
tatgcatcta cactctttcc ctacacgacg ctcttccgat cttttttacc tctg         54

<210> SEQ ID NO 30
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctcggcattc ctgctgaacc gctcttccga tcttttttttt tttttttttt tttt         54
```

METHOD AND SYSTEM FOR ENZYMATIC SYNTHESIS OF OLIGONUCLEOTIDES

CROSS-REFERENCE

This application claims the benefit of U.S. Provisional Patent Application No. 62/568,205, filed on Oct. 4, 2017 and U.S. Provisional Patent Application No. 62/727,174, filed on Sep. 5, 2018, which are entirely incorporated herein by reference.

SEQUENCE LISTING

The instant application contains a Sequence Listing which has been submitted electronically in ASCII format and is hereby incorporated by reference in its entirety. Said ASCII copy, created on Oct. 18, 2018, is named 38558-733_601_SL.txt and is 7,632 bytes in size.

BACKGROUND

Synthetic nucleic acids such as oligonucleotides play an important role in many fields including molecular biology, forensic science, and medical diagnostics. Oligonucleotides have become important tools in modem biotechnology and medical science. For example, oligonucleotides have been used in a wide variety of techniques, including, for example, diagnostic probing methods, PCR, antisense inhibition of gene expression, and nucleic acid assembly. Oligonucleotides synthesis may be involved in genome editing, such as applications relying on CRISPR, DNAzymes (i.e., catalytically active deoxynucleic acid (DNA) molecules that are obtained via in vitro selection), DNA origami, DNA for data storage, and spatial transcriptomics. The wide range of applications of oligonucleotides also led to the development of nucleic acid arrays, including, for example, deoxyribonucleic acid (DNA) and ribonucleic acid (RNA) arrays.

Designed nucleic acid sequences are assembled one at a time by joining the corresponding oligonucleotides (synthesized previously) using either the polymerase chain reaction (PCR) or the ligase chain reaction (LCR) approach. See, e.g., Smith et al., "Generating a synthetic genome by whole genome assembly: X174 bacteriophage from synthetic oligonucleotides," Proc. Natl. Acad. Sci. USA, 100(26): 15440-5 (2003). Gibson Assembly® is a molecular cloning method which allows for the joining of multiple DNA fragments in a single, isothermal reaction. See, e.g. Gibson et al., "Enzymatic assembly of DNA molecules up to several hundred kilobases". *Nature Methods.* 6 (5): 343-345. The construction of a long oligonucleotide requires simultaneous synthesis of multiple gene sequences. However, the state-of-the-art oligonucleotide synthesis is accomplished essentially on a one-by-one basis by chemical synthesis. See Zhou et al., "Microfluidic PicoArray synthesis of oligodeoxynucleotides and simultaneous assembling of multiple DNA sequences," Nucleic Acids Res., 11:32(18): 5409-17 (2004).

SUMMARY

It can be desirable to synthesize single-stranded, immobilized or solution-phase oligonucleotides by polymerase catalyzed reactions. The present disclosure provides processes for accomplishing this enzymatic synthesis by using an enzyme that requires no more than 7 base pairings to extend a single-stranded, immobilized oligonucleotide from its free 3' end. In some embodiments, the enzymatic synthesis requires 1, 2, 3, 4, 5, 6, or 7 base pairings to extend a single-stranded, immobilized oligonucleotide from its free 3' end. The present disclosure also provides processes for accomplishing this enzymatic synthesis by using modified polymerase that requires no more than 7 base pairings to extend a single-stranded, solution-phase oligonucleotide from its free 3' end. In some cases, the enzymatic synthesis requires 1, 2, 3, 4, 5, 6, or 7 base pairings to extend a single-stranded, solution phase oligonucleotide from its free 3' end.

In one aspect, the present disclosure provides a method of synthesizing a single-stranded oligonucleotide, comprising: (a) providing a single-stranded primer comprising a free 3' end, a polymerase, and a nucleotide reagent; and (b) extending the single-stranded primer from the free 3' end with the nucleotide reagent by the polymerase; and the polymerase requires no more than 7 base pairings to extend the single-stranded primer.

In some embodiments, the nucleotide reagent is a reversible terminator nucleotide bearing a 3' terminator. In some embodiments, the single-stranded primer further comprises a 5'-end attached to a substrate. In some embodiments, the polymerase is a modified polymerase. In some embodiments, the method further comprises: (c) removing the 3' terminator from the reversible terminator nucleotide. In some embodiments, the method further comprise: (d) repeating steps (a)-(c). In some embodiments, the repeating in (d) extends the single-stranded primer from the 3' free end, thereby synthesizing a single-stranded oligonucleotide product comprising the single-stranded primer.

In some embodiments, the method further comprises comprising, after (b) and before (c): (b1) treating the single-stranded primer with a dideoxy nucleotide reagent in the presence of the polymerase or a terminal deoxynucleotidyl transferase (TdT).

In some embodiments, the method further comprises after (a) and before (b): (a1) hybridizing a hybridization site on the single-stranded primer with a template, and the hybridization site is at the 3' end and comprises no more than 7 bases. In some embodiments, the template is the single-stranded primer, an adjacent single-stranded nucleic acid attached to the substrate, or a member of a plurality of single-stranded nucleic acid templates in solution. In some embodiments, the template is the adjacent single-stranded nucleic acid, and the adjacent single-stranded nucleic acid shares no more than 5%, no more than 10%, no more than 15%, no more than 20%, no more than 25%, no more than 30%, no more than 35%, no more than 40%, no more than 45%, no more than 50%, no more than 55%, no more than 60%, no more than 65%, no more than 70%, no more than 75%, no more than 80%, no more than 85%, no more than 90%, or no more than 95% sequence identity with the single-stranded primer. In some embodiments, the template is the adjacent single-stranded nucleic acid, and the adjacent single-stranded nucleic acid shares 100% sequence identity with the single-stranded oligonucleotide. In some embodiments, the adjacent single-stranded nucleic acid shares at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, sequence identity with the single-stranded primer. In some embodiments, the adjacent single-stranded nucleic acid shares about 25%, about 30%, about 35%, about 40%, about 45%, about 50%, about 55%, about 60%, about 65%, about 70%, about 75%, about 80%, about 85%, about 90%, or about 95% sequence identity with the single-stranded primer. In some embodiments, the adjacent single-stranded nucleic acid does not share sequence identity substantially with the single-stranded primer. In some embodiments, the plurality of single-stranded nucleic acid templates in solution are a plurality of dimers, a plurality of trimers, a plurality of tetramers, a plurality of pentamers, a plurality of hexamers, a plurality of heptamers, a plurality of octamers, a plurality of nonamers, a plurality of decamers, a plurality of undecamers, or a plurality of dodecamers. In some embodiments, the plurality of single-stranded nucleic acid templates in solution is a plurality of oligonucleotides having more than ten bases in length. In some embodiments, the plurality of single-stranded nucleic acid templates comprises random sequences.

In some embodiments, the hybridization site comprises 1, 2, 3, 4, 5, 6 or 7 bases. In some embodiments, efficiency of the extending in (b) is improved in the presence of the template in (al). In some embodiments, the polymerase requires 1, 2, 3, 4, 5, 6, or 7 base pairings to extend the single-stranded primer. In some embodiments, the extending is conducted between about 20° C. and about 99° C. In some embodiments, the extending is conducted between about 50° C. and about 75° C. In some embodiments, the extending is conducted between about 55° C. and about 65° C. In some embodiments, the extending is conducted at about 60° C. In some embodiments, the enzyme is a deoxyribonucleic acid (DNA) polymerase, an RNA polymerase, or a reverse transcriptase. In some embodiments, the modified deoxyribonucleic acid (DNA) polymerase is a thermophilic DNA polymerase having a decreased 3' to 5' proofreading exonuclease activity when compared to the unmodified DNA polymerase. In some embodiments, modified DNA polymerase has no more than 6% 3' to 5' proofreading exonuclease activity when compared to the unmodified DNA polymerase. In some embodiments, the modified DNA polymerase has no more than 1%, no more than 2%, no more than 3%, no more than 4%, or no more than 5% 3' to 5' proofreading exonuclease activity when compared to the unmodified DNA polymerase.

In some embodiments, the modified reverse transcriptase is Moloney murine leukemia virus (M-MLV) reverse transcriptase or human immunodeficiency virus type-1 reverse transcriptase. In some embodiments, modified reverse transcriptase is modified Moloney murine leukemia virus (M-MLV) reverse transcriptase or modified human immunodeficiency virus type-1 reverse transcriptase. In some embodiments, the enzyme may be modified to increase extension efficiency, increase efficiency with a 3'-modified substrate, or decrease temperature or pH sensitivity, etc. In some embodiments, the plurality of single-stranded nucleic acid templates comprises random sequences.

In some embodiments, the single-stranded primer comprises a uracil. In some embodiments, the method further comprises: cleaving the single-stranded primer at the uracil. In some embodiments, the uracil is at the last base at the 3' end of the single-stranded primer In some embodiments, the enzyme is a DNA polymerase. In some embodiments, the DNA polymerase is not modified. In some embodiments, the DNA polymerase is modified. In some embodiments, the enzyme is 9° Nm™ DNA Polymerase. In some embodiments, the enzyme is modified 9° Nm™ DNA Polymerase. In some embodiments, the modified 9° Nm™ DNA Polymerase shares at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, sequence identity with the 9° Nm™ DNA Polymerase (New England Biolabs, Inc.). In some embodiments, the modified 9° Nm™ DNA Polymerase shares about 25%, about 30%, about 35%, about 40%, about 45%, about 50%, about 55%, about 60%, about 65%, about 70%, about 75%, about 80%, about 85%, about 90%, or about 95%, sequence identity with the ° Nm™ DNA Polymerase (New England Biolabs, Inc.).

In some embodiments, the reverse transcriptase is Moloney murine leukemia virus (M-MLV) reverse transcriptase or human immunodeficiency virus type-1 reverse transcriptase. In some embodiments, the reverse transcriptase is modified Moloney murine leukemia virus (M-MLV) reverse transcriptase or modified human immunodeficiency virus type-1 reverse transcriptase. In some embodiments, the modified M-MLV reverse transcriptase shares at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, sequence identity with the M-MLV reverse transcriptase (Sigma Aldrich). In some embodiments, the modified M-MLV reverse transcriptase shares about 25%, about 30%, about 35%, about 40%, about 45%, about 50%, about 55%, about 60%, about 65%, about 70%, about 75%, about 80%, about 85%, about 90%, or about 95%, sequence identity with the M-MLV reverse transcriptase (Sigma Aldrich). In some embodiments, the modified reverse transcriptase is modified Moloney murine leukemia virus (M-MLV) reverse transcriptase or modified human immunodeficiency virus type-1 reverse transcriptase.

In some embodiments, the method repeats its steps such that the repeating extends the single-stranded primer from the 3' free end, thereby synthesizing a single-stranded oligonucleotide product comprising the single-stranded primer. In some embodiments, the method further comprises: further comprising: cleaving the single-stranded oligonucleotide product. In some embodiments, the method further comprises: cleaving the synthesized growing strand or hybridized complex. In some embodiments, the cleaving the synthesized growing strand or hybridized complex comprises using a restriction enzyme, using a cleavable linker in the synthesized growing strand or hybridized complex (e.g., a cleavable linker attached to the growing strand at the 5' end and between the growing strand and the 5' end of the strand, or using a transposase targeting a position at the 5' end. In some embodiments, the cleaving cleaves away the enzymatically synthesized oligonucleotide. In some embodiments, the cleaving cleaves within the enzymatically synthesized fragment of the growing strand/hybridizing complex and removes a templating oligonucleotide. In some embodiments, the cleaving cleaves within the universal templating oligos (UTO). In some embodiments, the cleaving cleaves at the 3'-end of the universal templating oligos (UTO). In some embodiments, the cleaving cleaves at a position within the single-stranded primer. In some embodiments, the cleaving removes a sequence comprises at least a part of the single-stranded primer. In some embodiments, the removed sequence comprises the single-stranded primer.

In some embodiments, the single-stranded primer comprises a uracil. In some embodiments, the method further comprises: cleaving the single-stranded primer at the uracil. In some embodiments, the uracil is at the last base at the 3' end of the single-stranded primer. In some embodiments, the modified polymerase requires 1, 2, 3, 4, 5, 6, or 7 base pairings to extend the single-stranded primer. In some embodiments, the modified polymerase requires 1, 2, 3, 4, 5, 6, or 7 base pairings to extend the single-stranded primer.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1a shows example processes for enzymatic oligonucleotide synthesis: (i) using a deoxynucleotidyl transferase, (ii) using a DNA/RNA polymerases and reverse transcriptase, and (iii) using a ligase.

FIG. 1b shows an example process for polymerase-mediated solid-phase oligonucleotide synthesis using chemically blocked substrates.

FIG. 1c shows an example denaturing PAGE analysis of extending a 20-base single-stranded oligonucleotide template by sequential incorporation of two bases having reversible terminators on its 3'-OH.

FIG. 1d shows an example of denaturing PAGE analysis of synthesizing a 20-base single-stranded DNA fragment (GCTGTATCGGCTGAATCGTA (SEQ ID NO: 1)) based on a universal templating oligonucleotide using Duplase-3.

FIG. 2a discloses SEQ ID NOS 2, 2, 2, 2, 2, 2, 7 and 8, respectively, in order of appearance.

FIG. 3a discloses SEQ ID NOS 2, 2, 2, 2, 2, 2, 2 and 9-11, respectively, in order of appearance.

FIG. 3b discloses SEQ ID NOS 5, 5, 5, 5, 6 and 5, respectively, in order of appearance.

FIG. 4a shows the fidelity of extension products on a double-stranded substrate using denaturing PAGE in the presence of deoxyadenosine triphosphate (dATP), deoxythymidine triphosphate (dTTP), deoxycytidine triphosphate (dCTP), or dGTP as the substrate and Duplase-1 (as in (i)), Duplase-2 (as in (ii)), or Duplase-3 (as in (iii)). FIG. 4a discloses SEQ ID NOS 12 and 8, respectively, in order of appearance.

FIG. 4b shows the fidelity of extension products on a single-stranded 20 base substrate (CACTGATTACCCTA-CACGAG (SEQ ID NO: 2)) using denaturing PAGE in the presence of 3'-O-azidomethyl-dATP, 3'-O-azidomethyl-dTTP, 3'-O-azidomethyl-dCTP, or 3'-O-azidomethyl-dGTP as the substrate and Duplase-1 (as in (i)), Duplase-2 (as in (ii)), or Duplase-3 (as in (iii)). FIG. 4b discloses SEQ ID NOS 2, 2, 13 and 2, respectively, in order of appearance.

FIG. 6 discloses SEQ ID NOS 2, 2, 13 and 2, respectively, in order of appearance.

FIG. 8b discloses SEQ ID NO: 14 as "TTTTTTTTTTTTTTTTTT".

FIG. 10 shows a table of examples of oligo sequences used in experiments and figures disclosed herein. FIG. 10 discloses SEQ ID NOS 15-26, 23 and 27-30, respectively, in order of appearance.

DETAILED DESCRIPTION

Figure 2A:
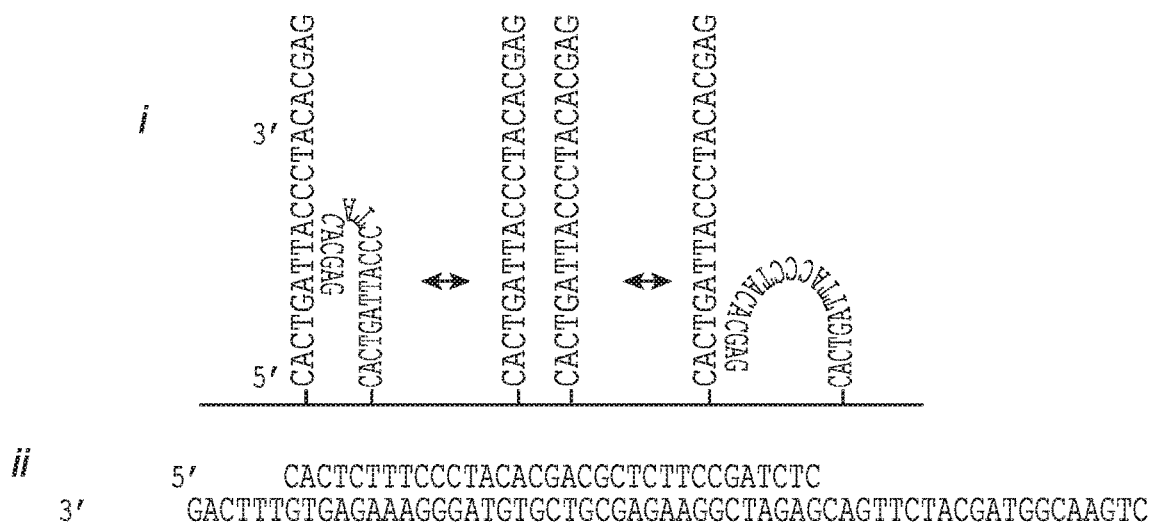
FIG. 2a shows an example of two templates used for extension reactions with M-MLV reverse transcriptases (RTs) and deoxyribonucleoside triphosphates (dNTPs) or 3'-O-azidomethyl dNTPs using (i) a 20-base single-stranded solid phase oligo; or (ii) a 33-base primer hybridized to a template.

The present disclosure provides processes for the enzymatic synthesis of single-stranded, immobilized or solution-phase oligonucleotide. The processes disclosed herein may use modified or unmodified enzymes, including, for example, polymerase, which requires no more than 7 base pairings to extend an immobilized or solution-phase primer. The processes disclosed herein may use a template during the extension reactions for the immobilized or solution-phase primer by the modified or unmodified polymerase. In some embodiments, the processes disclosed herein uses modified polymerase. In some embodiments, the processes disclosed herein may use a template during the extension reactions for the immobilized primer by the modified polymerase.

Currently the demand for longer and more accurate oligonucleotides is increasing as DNA and RNA are used for new applications in therapeutics, high-throughput genotyping, synthetic biology, and data storage, for example. These new applications place high requirements on stepwise yields, but current chemical synthesis methods can achieve about 98.5-99.5% stepwise efficiency. The environment required for chemical reactions in non-enzymatic synthesis may be incompatible with photoresist chemistry, limiting the level of intricacy that can be built into an array See McGall et al., "Light-directed synthesis of high-density oligonucleotide arrays using semiconductor photoresists," Proc. Natl. Acad. Sci. USA, 93: 13555-60 (1996). Furthermore, oligo synthesis is responsible for more than 300,000 gallons of hazardous chemical waste annually, placing additional demand for the development of enzymatic methods. See LeProust et al., "Synthesis of high-quality libraries of long (150mer) oligonucleotides by a novel depurination controlled process," Nucleic Acids Res., 38(8): 2522-40 (2010). Accordingly, there is an unmet need for enzymatic synthetic method for the synthesis of oligonucleotides.

The terminology used herein is for the purpose of describing particular cases only and is not intended to be limiting. As used herein, the singular forms "a", "an" and "the" can be intended to include the plural forms as well, unless the context clearly indicates otherwise. Furthermore, to the extent that the terms "including", "includes", "having", "has", "with", or variants thereof can be used in either the detailed description and/or the claims, such terms can be intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean about plus or minus 10%, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values may be described in the application and claims, unless otherwise stated the term "about" meaning within an acceptable error range for the particular value should be assumed. Also, where ranges and/or subranges of values are provided, the ranges and/or subranges can include the endpoints of the ranges and/or subranges.

The term "substantially" as used herein can refer to a value approaching 100% of a given value. For example, an active agent that is "substantially localized" can indicate that about 90% by weight of an active agent, salt, or metabolite can be present relative to a total amount of an active agent, salt, or metabolite. In some cases, the term can refer to an amount that can be at least about 90%, 91%, 92%, 93%, 94%, 95%, 96%, 97%, 98%, 99%, 99.9%, or 99.99% of a total amount. In some cases, the term can refer to an amount that can be about 100% of a total amount.

As used herein, nucleotides are abbreviated with 3 letters. The first letter indicates the identity of the nitrogenous base (e.g. A for adenine, G for guanine), the second letter indicates the number of phosphates (mono, di, tri), and the third letter is P, standing for phosphate. Nucleoside triphosphates that contain ribose as the sugar, ribonucleoside triphosphates, are conventionally abbreviated as NTPs, while nucleoside triphosphates containing deoxyribose as the sugar, deoxyribonucleoside triphosphates, are abbreviated as dNTPs. For example, dATP stands for deoxyribose adenine triphosphate. NTPs are the building blocks of RNA, and dNTPs are the building blocks of DNA. In some cases, nucleotides are abbreviated with 2 letters. For example, dA represents dATP, and N3-dA represents 3'-O-azidomethyl-dATP. In some cases, other modified sugars may be used in the growing strand synthesis as well. For example, xeno nucleic acid (XNA) is a synthetic alternative to the natural nucleic acids DNA and RNA as information-storing biopolymers that differs in the sugar backbone. XNA type of research may include the types of synthetic XNA, such as, for example, 1,5-anhydrohexitol nucleic acid (HNA), cyclohexene nucleic acid (CeNA), threose nucleic acid (TNA), glycol nucleic acid (GNA), locked nucleic acid (LNA), and peptide nucleic acid (PNA).

The term "oligonucleotide" as used herein generally refers to a nucleotide chain. In some cases, an oligonucleotide is less than 200 residues long, e.g., between 15 and 100 nucleotides long. In some cases, the oligonucleotide can comprise at least or about 1, 2, 3, 4, 5, 6, 7, 8, 9, 10, 15, 20, 25, 30, 35, 40, 45, 50, 60, 70, or 90 bases. In some cases, the oligonucleotide can comprise at least or about 100, 200, 300, 400, 500, 600, 700, 800, 900, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 20,000, 30,000, 40,000, 50,000, 60,000, 70,000, 80,000, 90,000, 100,000, 200,000, 300,000, 400,000, 500,000, 600,000, 700, 000, 800,000, 900,000, 1,000,000, 2 million, 3 million, 4 million, 5 million, 6 million, 7 million, 8 million, 9 million, or 10 million bases. In some cases, the oligonucleotide can comprise more than 100, 200, 300, 400, 500, 600, 700, 800, 900, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2 million, 3 million, 4 million, 5 million, 6 million, 7 million, 8 million, 9 million, or 10 million bases. The oligonucleotides can be from about 3 to about 5 bases, from about 1 to about 50 bases, from about 8 to about 12 bases, from about 15 to about 25 bases, from about 25 to about 35 bases, from about 35 to about 45 bases, or from about 45 to about 55 bases. The oligonucleotide (also referred to as "oligo") can be any type of oligonucleotide (e.g., a primer). Oligonucleotides can comprise natural nucleotides, non-natural nucleotides, or combinations thereof.

The term "immobilization" as used herein generally refers to forming a covalent bond between two reactive groups. For example, polymerization of reactive groups is a form of immobilization. A Carbon to Carbon covalent bond formation is an example of immobilization. In some cases, the term "immobilization," when discussing attaching a biological molecule, such as, for example, a DNA or RNA or oligonucleotide, to solid supports can be accomplished using chemical bonds including, but not limited to, covalent bonds. For example, in some cases, such attaching comprises I-Linker™, amine-modified oligos covalently linked to an activated carboxylate group or succinimidyl ester, thiol-modified oligos covalently linked via an alkylating reagent such as an iodoacetamide or maleimide, Acrydite™-modified oligos covalently linked through a thioether, digoxigenin NHS ester, cholesterol-TEG, biotin-modified oligos captured by immobilized streptavidin, etc. See "Strategies for Attaching Oligonucleotides to Solid Supports" (available at "sfvideo.blob.core.windows.net/sitefinity/docs/default-source/technical-report/attaching-oligos-to-solid-supports.pdf?sfvrsn=47483407_6," retrieved on Sep. 14, 2018).

In methods and systems of the present disclosure, primers can be attached to a solid substrate. Primers can be bound to a substrate directly or via a linker. Linkers can comprise, for example, amino acids, polypeptides, nucleotides, oligonucleotides, or other organic molecules that do not interfere with the functions of probes. Primers or linkers may comprise cleavable groups. For example, the primer may comprise a uracil base. Deoxyuridine (dU) can be substituted for dT in DNA oligonucleotides. The base (dU) can be removed by the enzyme uracil-N-deglycosylase (UNG) which renders the oligo susceptible to strand scission at the dU site. In addition, a USER (Uracil-Specific Excision Reagent) Enzyme may generate a single nucleotide gap at the location of a uracil. USER Enzyme may be a mixture of Uracil DNA glycosylase (UDG) and the DNA glycosylase-lyase Endonuclease VIII. UDG may catalyze the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released.

In some cases, the methods and systems of the present disclosure comprises using primers not attached to a solid substrate, but staying in the solution phase.

The solid substrate can be biological, non-biological, organic, inorganic, or a combination of any of these. The substrate can exist as one or more particles, strands, precipitates, gels, sheets, tubing, spheres, containers, capillaries, pads, slices, films, plates, slides, or semiconductor integrated chips, for example. The solid substrate can be flat or can take on alternative surface configurations. For example, the solid substrate can contain raised or depressed regions on which synthesis or deposition takes place. In some examples, the solid substrate can be chosen to provide appropriate light-absorbing characteristics. For example, the substrate can be a polymerized Langmuir Blodgett film, functionalized glass (e.g., controlled pore glass), silica, titanium oxide, aluminum oxide, indium tin oxide (ITO), Si, Ge, GaAs, GaP, $SiO_2$, $SiN_4$, modified silicon, the top dielectric layer of a semiconductor integrated circuit (IC) chip, or any one of a variety of gels or polymers such as (poly)tetrafluoroethylene, (poly)vinylidenedifluoride, polystyrene, polycarbonate, polydimethylsiloxane (PDMS), polymethylmethacrylate (PMMA), polycyclicolefins, or combinations thereof.

Solid substrates can comprise polymer coatings or gels, such as a polyacrylamide gel or a PDMS gel. Gels and coatings can additionally comprise components to modify their physicochemical properties, for example, hydrophobicity. For example, a polyacrylamide gel or coating can comprise modified acrylamide monomers in its polymer structure such as ethoxylated acrylamide monomers, phosphorylcholine acrylamide monomers, betaine acrylamide monomers, and combinations thereof.

Enzymatic Synthesis of Oligonucleotides

In some cases, enzymatic oligo synthesis methods to extend a surface-bound single-stranded oligonucleotide may be performed in the presence of a reversible terminator nucleic acid as shown in FIG. 1a-1d. The term "reversible terminator nucleic acid" or "reversible terminator" as used herein generally refers to a modified nucleotide analog that can terminate primer extension reversibly. For example, a reversible terminator can be a modified nucleic acid which contains a covalent modification (for example on its 3'-OH group) to preclude further synthesis steps by the polymerase enzyme once the modified nucleic acid has been incorporated into the growing stand. This covalent modification can then be removed later, for instance using chemicals or specific enzymes, to allow the next complementary nucleotide to be added by the polymerase. As shown in FIG. 1a, methods for solid-phase enzymatic oligonucleotide synthesis can be achieved through different methods employing different kinds of enzymes that function on DNA and RNA. Depicted in FIG. 1a are (i) terminal deoxynucleotidyl transferase (TdT), (ii) DNA/RNA polymerases and reverse transcriptases, and (iii) ligases. Other enzymes with nucleotidyl transferase activities that can be used in the present disclosure to synthesize the growing strand include, for example, polynucleotide phosphorylase (PNPase), which is a bifunctional enzyme with a phosphorolytic 3' to 5' exoribonuclease activity and a 3'-terminal oligonucleotide polymerase activity.

In some cases, enzymatic oligo synthesis methods to extend a solution-phase single-stranded oligonucleotide may be performed in the presence of a reversible terminator nucleic acid and an enzyme configured to extend the solution-phase single-stranded oligonucleotide.

FIG. 1b details the processes for a DNA polymerase to extend a surface-bound single-stranded oligonucleotide. DNA polymerase may catalyze the incorporation of a reversible terminator onto a surface-bound single-stranded oligo (i.e., the starting primer). As shown in FIG. 1b(i), the templating strand may be the nascent strand itself through hairpin formation and cis-extension, a neighboring strand to hybridize with the nascent strand, or another oligo in solution to hybridize with the nascent strand. The surface-bound single-stranded oligo cannot be extended beyond a single base addition due to the presence of a 3'-OR blocking group (or terminating group) on the newly added nucleotide. After the single incorporation event, the 3'-hydroxyl may be restored through a cleavage event. This process may now be repeated for the addition of a second, third, etc. base.

In some cases, chemically-cleavable reversible terminators, 3'-O-azidomethyl-dNTPs, may be used, and deprotection may be achieved using tris(2-carboxyethyl) phosphine hydrochloride (TCEP). Other reversible terminators may be used as well, including, for example, enzymatically cleavable, acid- or base-labile linkers that are cleavable at selected pH, or UV-cleavable nucleotides, or aminoxy reversible terminators. Other reducing reagent may work to cleave the reversible terminators, 3'-O-azidomethyl-dNTPs after their incorporation into the growing strand.

DNA/RNA polymerases and reverse transcriptases require a double-stranded substrate to extend a nascent strand. In some cases, a method is disclosed herein to synthesize DNA or RNA sequences using a primer and a compatible DNA polymerase. In some cases, a DNA polymerase that requires base pairing for a few bases, for example, as low as requiring 1, 2, 3, 4, 5, or 6, base for pairing, may be used to drive the addition of nucleotides to extend the primer. In some cases, a primer may be hybridized with a universal template (that contains all possible combination of 3 base sequences). Single-base addition can be controlled through the use of a modified nucleotide substrate such as a reversible terminator. For example, since the polymerase used may only require two base pairings at the 3' end of the primer to allow the addition of a single nucleotide, if the third base on the template (immediately adjacent to the paired base pairs, for example, T) is complementary to the desired base (for example, A) to be added, the desired nucleotide (for example, dATP) can be processed by the DNA polymerase and add the base A to extend the primer (as shown in FIG. 1b(ii), R is the terminator, such that the nascent brand cannot be extended further). However, if the third base on the template (for example G) is not the desired complementary base (for example, T) and the only substrate base available is a modified dATP reversible terminator, the enzyme may incorporate the base A because of a misincorporation reaction or may not extend the primer under this condition. However, because the template may have other possible hybridization sites available and the primer/template complex may undergo rounds of dissociation/association, the primer may form the correct configuration with the template, under appropriate hybridization conditions, with a different template sequence. Therefore, this process of denaturing and hybridizing may repeat until the primer is hybridized with a template sequence to allow the polymerase to bind and then extend one base (for example, A) in the desired sequence. For example, if the desired base to add is "A", and if the template contains the following sequences: TNN (e.g., the template sequence is: TTTT-TACCTCTGTATGCATCGATAGGTCCGGGAAGCC-CACAAACTAATTTCAGAG TGACGT-TACTTGGCGCTTTTTT (SEQ ID NO: 4)), the primer may hybridize transiently with the template at high temperature. After the primer is hybridized with a subsequence that has T as the next unhybridized base (i.e., the third base discussed above), the DNA polymerase can then process dATP reversible terminator in the solution and extend the prime with a new base A bearing a terminator group at 3' position. In some cases, UTO may include a universal base, such as 5-nitroindole (5-NI) or 7-nitroindole (7-NI) analogs. In some cases, UTO may include two, three, or more than three universal bases. A "universal base" as used herein may refer to a base that can pair with all four canonical bases from the natural nucleotides. Universal bases may pair indiscriminately with any other base. Examples may include 2'-deoxyinosine (hypoxanthine deoxynucleotide) derivatives, nitroazole analogues, nitroindole analogues, and hydrophobic aromatic non-hydrogen-bonding bases (strong stacking effects).

Then the terminator group at 3' position can be removed (shown in FIG. 1b(iii), OH is the 3' OH, which can be further extended by the polymerase or other enzymes). Thereafter, the next desired base can be added to the free 3' OH just unmasked by repeating the above process. In some cases, the template itself can also serve as the primer, referred to as a self-priming oligo (SPO) or universal templating oligo (UTO). The primer can also start with or comprise a base that can be cut, for example, a U base. This would allow the cutting of the synthesized sequence at the "U" position from the primer such that the immobilized sequence can be removed from the solid substrate the prime bound to.

FIG. 1c shows the results of the sequential incorporation of two bases using reversible terminators on a 20-base single-stranded oligo on a solid surface. Denaturing PAGE analysis of the 20-base template (after incorporation of 3'-O-azidomethyl-dTTP (+1 base), followed by cleavage of the 3'-O-azidomethyl capping group and incorporation of 3'-O-azidomethyl-dCTP (+2 bases). The sign * indicates unextended control. FIG. 1d shows the results of the synthesis of a 20-base single-stranded DNA fragment on a universal templating oligo. Denaturing PAGE analysis may be conducted after the addition of 4, 8, 12, 16, and 20 bases during the synthesis of the 20-base sequence, GCTGTATCGGCTGAATCGTA (SEQ ID NO: 1), on a universal templating oligo using Duplase-3. The sign * indicates unextended control.

In some cases, the extension methods of the present application may allow the synthesis a substrate-bound, single-stranded nucleic acid sequence in the presence of an enzyme without the presence of a full-length complementary template. In some cases, the extension method of the present application may allow the synthesis a substrate-bound, single-stranded nucleic acid sequence in the presence of an enzyme when the longest complementary sequences in the template with regard to the synthesized, substrate-bound, single-stranded nucleic acid sequence are 1, 2, 3, 4, 5, or 6 bases long and the longest complementary sequence in the template is shorter than the full length of the synthesized, substrate-bound, single-stranded nucleic acid sequence. In some cases, the longest complementary sequence in the template is at least 3, 4, 5, 6, 7, 8, 9, 10, 11, 12, 13, 14, 15, 16, 17, or 18-base shorter than the full length of the synthesized, substrate-bound, single-stranded nucleic acid sequence when the full length of the substrate-bound, single-stranded nucleic acid sequence is counted from the very first added base to the primer (i.e., starting from the first base added by the first extension reaction and ended with the last base added by the final extension reaction). In some cases, there is a complementary sequence in the template for any three consecutive bases in the synthesized, substrate-bound, single-stranded nucleic acid sequence. In some cases, there is a complementary sequence in the template for any four consecutive bases in the synthesized, substrate-bound, single-stranded nucleic acid sequence. In some cases, there is a complementary sequence in the template for any five consecutive bases in the synthesized, substrate-bound, single-stranded nucleic acid sequence. In some cases, there is a complementary sequence in the template for any six consecutive bases in the synthesized, substrate-bound, single-stranded nucleic acid sequence.

Enzymes for the Extension Reactions

Extension reactions using reversible terminators may require enzymes whose catalytic domains are sufficiently large to accommodate the 3'-capping group. Some modified DNA polymerases may be developed for this purpose. For example, reverse transcriptases (RTs) may possess a template-switching "clamping" ability that is the basis of SMART cDNA synthesis. Moloney murine leukemia virus (M-MLV) RT and human immunodeficiency virus type-1 RT may require just two bases of hybridization for this activity, and M-MLV RT can incorporate reversible terminators on double-stranded DNA in primer extension reactions. SMART template switching may require non-templated addition of nucleotides to the 3' end of newly synthesized cDNA by using manganese as a divalent ion cofactor to enhance its activities. For example, M-MLV reverse transcriptases, SuperScript IV and SMARTScribe, may incorporate native dNTPs on single-stranded DNA (FIG. 2). M-MLV RTs may incorporate reversible terminators. Both SuperScript IV and SMARTScribe may be able to incorporate 3'-O-azidomethyl reversible terminators on double-stranded DNA templates, but they may not be able to incorporate reversible terminators on single-stranded templates.

Figure 2B:
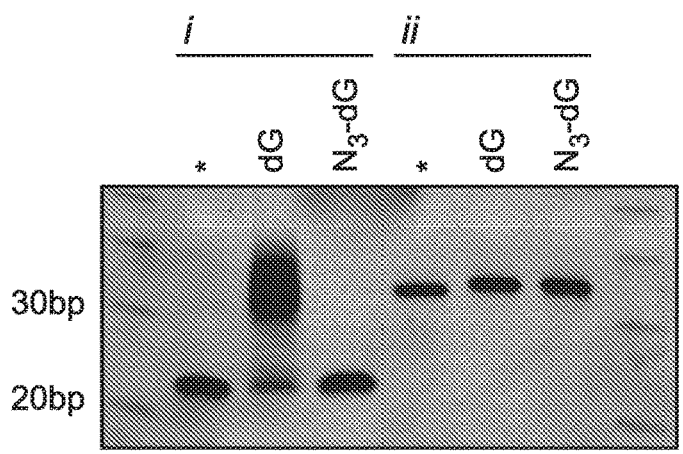
FIG. 2b shows denaturing PAGE analysis of extension products (i) using Superscript IV M-MLV RT on single-stranded DNA shown in FIG. 2a(i); or (ii) using Superscript IV M-MLV RT on double-stranded DNA shown in FIG. 2a(ii).
Figure 2C:
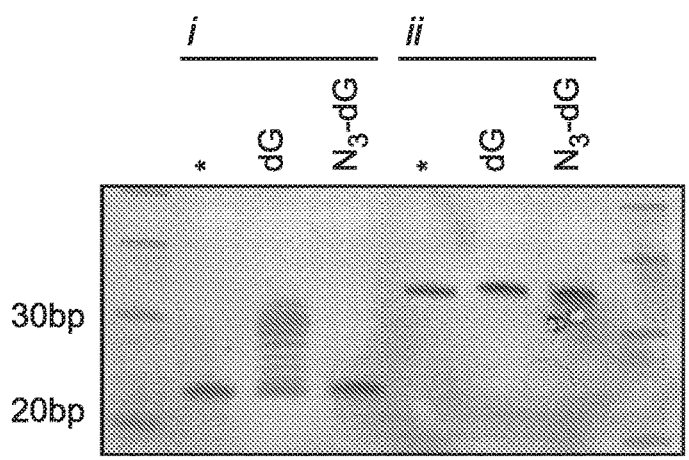
FIG. 2c shows denaturing PAGE analysis of extension products (i) using SMARTScribe RT on single-stranded DNA shown in FIG. 2a(i); or (ii) using SMARTScribe RT on double-stranded DNA shown in FIG. 2a(ii)

FIG. 2 shows that M-MLV Reverse Transcriptases (RTs) can incorporate dNTPs on single-stranded DNA, and M-MLV RTs are capable of using reversible terminators as substrates. In some cases, M-MLV RTs may be modified to incorporate reversible terminators. In some cases, an unmodified M-MLV RT may not incorporate 3'-O-azidomethyl dNTPs as efficiently as a modified M-MLV RT. In some cases, M-MLV RTs incorporate reversible terminators. FIG. 2a shows DNA sequences tested for extension with M-MLV RTs. Extension can be assayed using either a 20 base single-stranded solid phase oligo (shown in FIG. 2a(i)), or a 33 base primer hybridized to a template (shown in FIG. 2a(ii)). Both sequences may use template to test the incorporation of guanosine. FIG. 2b shows the results from the extension with Superscript IV. FIG. 2b(i) shows that Superscript IV can incorporate dGTP but not 3'-O-azidomethyl-dGTP on single-stranded DNA. FIG. 2b(ii) shows that using the same reaction conditions in FIG. 2b(i), extension can be seen with both types of nucleotides on double-stranded DNA. The sign * indicates unextended control. FIG. 2c shows the results of the extension with SMARTScribe. FIG. 2c(i) shows that SMARTScribe can incorporate dGTP but not 3'-O-azidomethyl-dGTP on single-stranded DNA. FIG. 2c(ii) shows that using the same reaction conditions in FIG. 2c(i), extension can be seen with both types of nucleotides on double-stranded DNA. The sign * indicates unextended control.

In some cases, modified 9° N™ DNA polymerases, which are capable of extending a single-stranded primer on a solid surface using a reversible terminator as the source of new base, are used. In some cases, the oligo serves as both the primer and the template. In some cases, such a modified 9° N™ DNA polymerase can be referred to as a Duplase (available at Centrillion Technologies, Palo Alto, Calif.). Duplases may only require hybridization of two bases for extension (FIG. 3). For example, Duplase-1 (also referred to as CENT1, see US20160355541) can efficiently incorporate reversible terminators along a double-stranded DNA substrate in reaction times as short as one minute when nucleotide concentrations are as low as 2 µM in solution. Longer extension times and higher nucleotide concentrations may be required for extensions of single-stranded oligos.

Figure 3A:
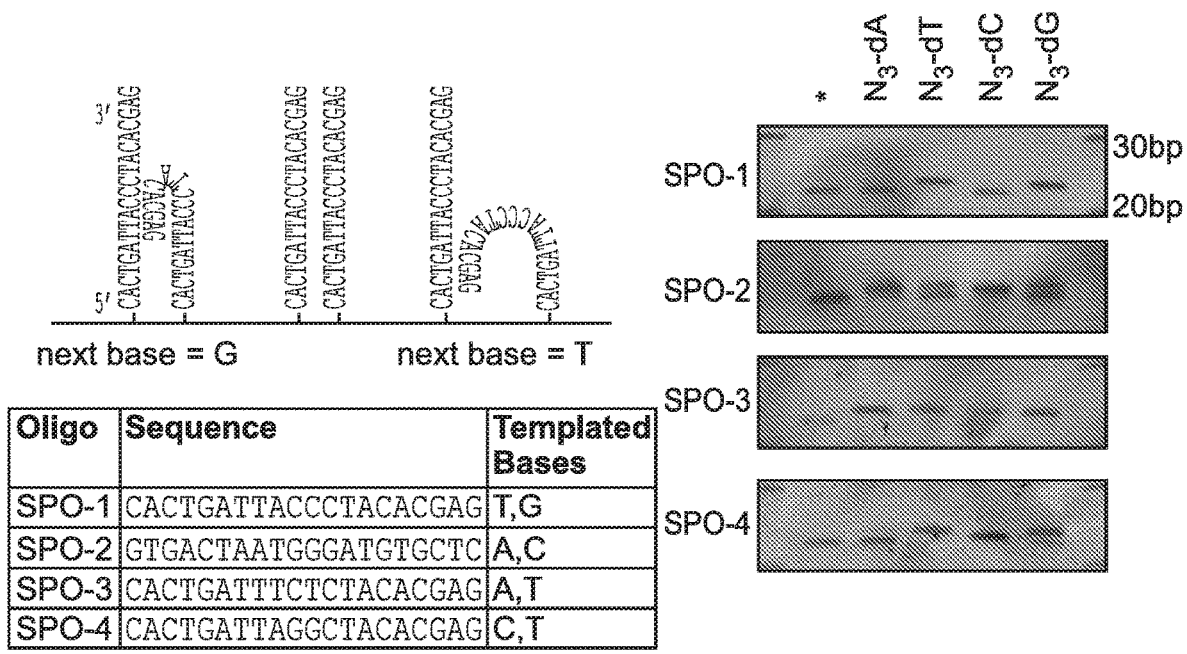
FIG. 3a shows examples of sequence-specific extension of single-stranded DNA using four 20-base single-stranded sequences as both a primer and a template in reactions with Duplase-3.
Figure 3B:
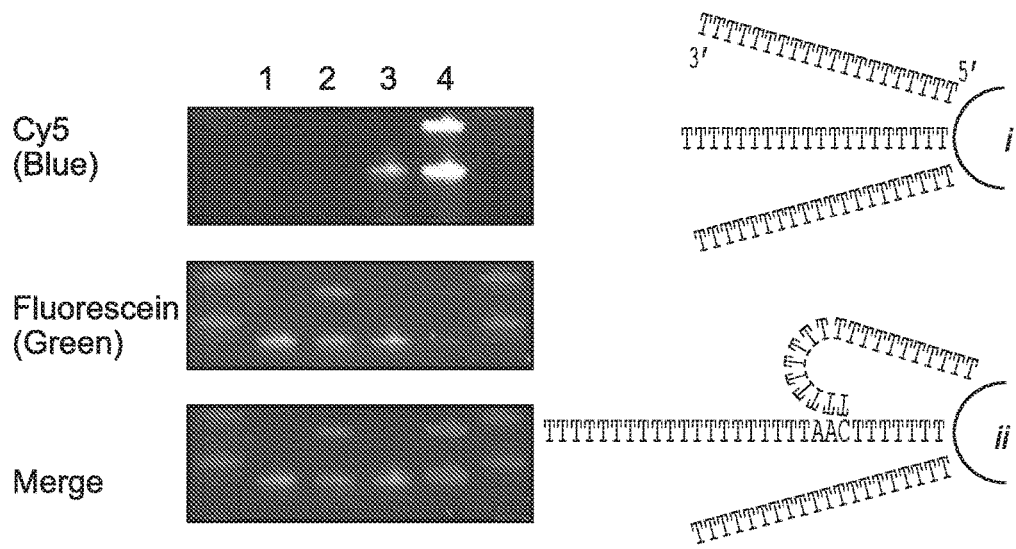
FIG. 3b shows examples of extending surface-bound oligonucleotides through intermolecular reactions a 20 base poly-T sequence next to a neighboring 30 base poly-T sequence with an internal CAA to which the poly-T sequence can hybridize (two bases) and be extended using deoxyguanosine triphosphate (dGTP).

As shown in FIG. 3a, sequence-specific extension of single-stranded DNA may be accomplished by Duplase-3, another example of the Duplase. Also shown is the denaturing PAGE analysis of four 20-base sequences that serve as both primer and template in reactions with Duplase-3 and 3'-O-azidomethyl-dNTPs. The self-priming oligos (SPO) are named SPOs 1-4 for these self-priming reactions. Duplase-3 may extend the oligos with bases templated by the hybridization of just the final two 3' bases on the primer. The sign * indicates unextended control. As shown in FIG. 3b, the extension of surface-bound oligos may be accomplished through intermolecular reactions. Oligos with the sequences TTTTTTTTTTTTTTTTTTTT (20-bases) (SEQ ID NO: 5) and TTTTTTTCAAT-TTTTTTTTTTTTTTTTTTT (30-bases) (SEQ ID NO: 6) may be immobilized on magnetic beads as illustrated on the right side of FIG. 3b, using either one oligo or both on the same bead. Samples can be analyzed by denaturing PAGE (see the left side of FIG. 3b). Lanes 1 and 3 can use beads shown as (i) on the right. Lanes 2 and 4 may use beads shown as (ii) on the right. Lanes 1 and 2 can be control samples not extended using Duplase-3. Lanes 3 and 4 can be extended using Duplase-3 and Cy5-ddGTP. All samples can then be labeled with terminal deoxynucleotidyl transferase (TdT) and fluorescein-12-ddUTP so that any primer not extended with Cy5-ddGTP may be labeled with fluorescein. As shown in lane 3 on the denaturing PAGE gel, Duplase-3 may not efficiently extend the 20-base poly-T sequence. However, as shown in lane 4, when the 30 base sequence, TTTTTTTCAATTTTTTTTTTTTTTTTTTTT (SEQ ID NO: 6), is immobilized on the same surface as the 20-base poly-T oligo, extension signal of the 20-mer is robust on the denaturing PAGE gel. This may demonstrates how to synthesize a surface-bound oligo attached by a poly-T linker to the support in the presence of adjacent templating oligos; and the templating oligos can be cleaved away after the synthesis of the growing strand.

FIG. 3 shows that intermolecular reactions alone may facilitate extension of surface-bound oligos. Poly-T sequences may not hybridize with other poly-T sequences. When the surface-bound oligo are only poly-T sequences, extension may be limited. However, robust extension may be achieved when a second templating oligo is also bound to the same surface such that the poly-T sequence can hybridize to the neighboring second templating oligo.

Comparative analysis of the fidelity of the three Duplase enzymes is shown in FIG. 4. FIG. 4a shows fidelity on a double-stranded substrate. The primer extension reactions can be conducted using the two oligo sequences shown in FIG. 4a. The shorter sequence is the primer and the longer sequence is the template immobilized on the substrate. After the extension reactions are completed, the shorter primer strand, which have been extended, can be stripped from the surface-bound template and analyzed by denaturing PAGE. As shown in FIG. 4a, extension opposite adenine is conducted in the presence of dATP, dTTP, dCTP, or dGTP as the substrate and Duplase-1 (as in (i)), Duplase-2 (as in (ii)), or Duplase-3 (as in (iii)). Decreasing fidelity can be observed in the denaturing PAGE gel from Duplase-1 to Duplase-2 to Duplase-2. The sign * indicates unextended primer control. FIG. 4b shows the extension of a single-stranded substrate using three different duplases. The extension reactions can be conducted using a surface-bound single-stranded oligo as shown in FIG. 4b with 3'-O-azidomethyl-dATP, 3'-O-azidomethyl-dTTP, 3'-O-azidomethyl-dCTP, or 3'-O-azidomethyl-dGTP in solution, and in the presence Duplase-1 (as in (i)), Duplase-2 (as in (ii)), or Duplase-3 (as in (iii)). The sign * indicates unextended primer control. As polymerase fidelity decreases, the capability to incorporate bases not templated by a neighboring strand or a hairpin structure may increase. Traditional primer extension reactions in FIG. 4a show that Duplase-1 is higher fidelity than Duplase-2, which is in turn higher fidelity than Duplase-3. Decreasing enzyme fidelity increases the probability of misincorporation or wrong incorporation events, thus increasing the chance that a non-templated base may be added to a short surface-bound oligo. The more promiscuous the enzyme, the higher the yield of the reaction product from the single-stranded primer may be. Duplase-3 may be used for the controlled synthesis of the single-stranded nucleic acid sequence.

Figure 5:
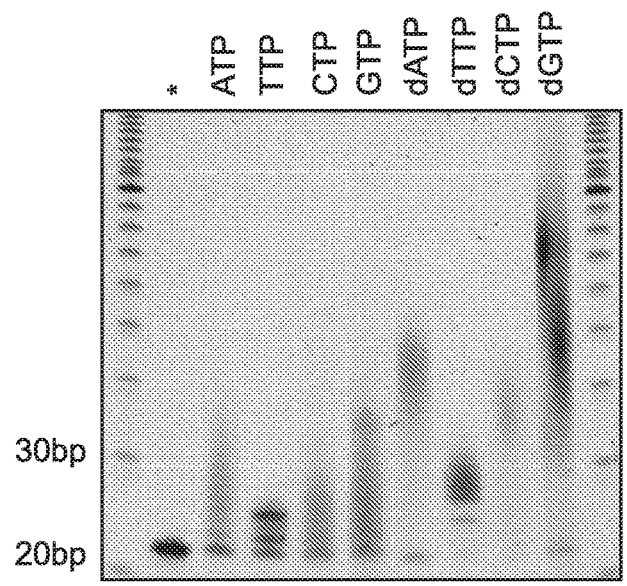
FIG. 5 shows an example of denaturing PAGE analysis of Duplase-3 to incorporate ribonucleotide on a 20-base single-stranded oligonucleotide.

Furthermore, Duplases can use ribonucleotides as a substrate (see FIG. 5), thereby synthesizing single-stranded RNA sequences. As shown in FIG. 5, Duplase-3 can incorporate ribonucleotides on a single-stranded oligo. FIG. 5 shows the denaturing PAGE analysis of a 20 base single-stranded surface-bound oligo extended with Duplase-3 in the presence of NTPs or dNTPs. The sign * indicates unextended control. In some cases, polymerases, including, for example, Duplaces, can incorporate non-natural bases, or nucleotide comprising different sugar backbones than native sugar backbones, modified nucleotides such as fluorescence-labeled dNTPs or biotinylated dNTPs, or thio-modified dNTPs, etc.

Extension Reaction Conditions

For the extension reactions to work, misincorporation may lead to an increased rate of extension with the nucleotide added in solution. There may be variables of the extension reaction conditions which may increase the chance of misincorporation. For example, reaction temperatures and the metal ion used may have some impact. Manganese, for example, may alter the geometry of the polymerase's substrate binding pocket, thereby opening it up to allow for polymerization with a non-templated base. In addition, polymerases may be temperature sensitive with respect to fidelity in that a higher reaction temperature may lead to low fidelity and higher rate of incorporation. Duplases may be thermophilic, with activity increasing with increasing reaction temperatures up to about 75° C.

Figure 6:
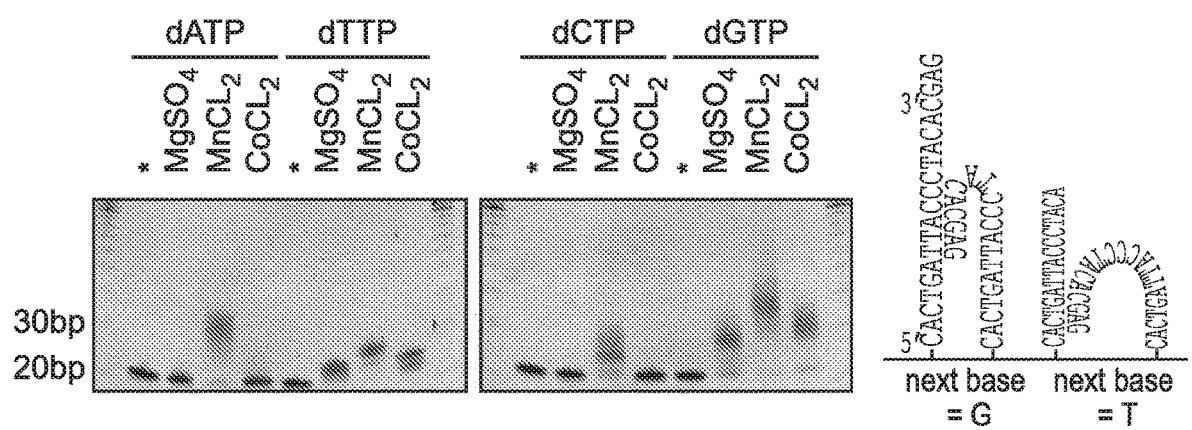
FIG. 6 shows an example of denaturing PAGE analysis of Duplase-3 to incorporate nucleotide on a 20-base single-stranded oligonucleotide in the presence of different divalent metals.

FIG. 6 shows that extension of single-stranded oligos can be achieved using different divalent ions. Single-stranded oligo synthesis reactions may be conducted in the presence of different divalent metals. Denaturing PAGE analysis of a 20-base single-stranded surface-bound oligo extended with Duplase-3 and dATP, dTTP, dCTP, and dGTP may show different extension results when using magnesium, manganese, or cobalt ions as a cofactor in the reaction solution. As shown in FIG. 6, extension of templated bases can be achieved with all three metals. But extension of non-templated bases may be achieved with manganese ion.

Figure 7A:
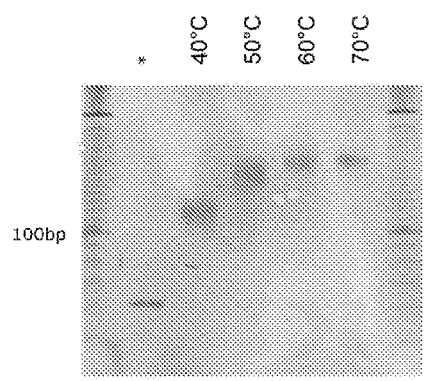
FIG. 7a shows an example of denaturing PAGE analysis of Duplase-3 to incorporate nucleotide on a 59-base single-stranded oligonucleotide at different temperatures in the absence of a template in solution.
Figure 7B:
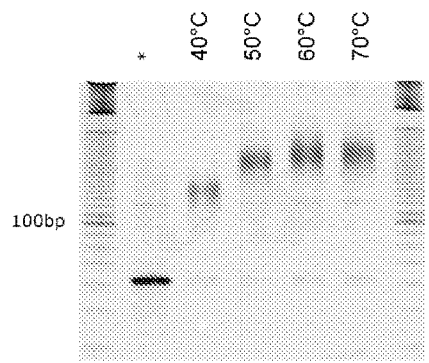
FIG. 7b shows an example of denaturing PAGE analysis of Duplase-3 to incorporate nucleotide on a 59-base single-stranded oligonucleotide at different temperatures in the presence of 3'-phosphate blocked random hexamer templates in solution.
Figure 8A:
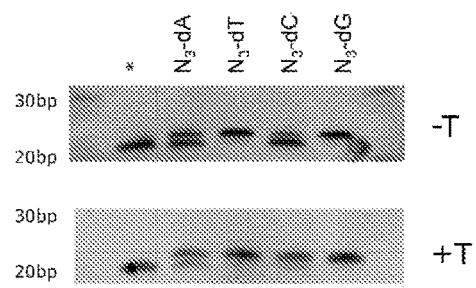
FIG. 8a shows an example of denaturing PAGE analysis of extension of a short solid-phase oligo by Duplase-3 is enhanced by the addition of randomers to the reaction solution. The symbol "−T" means without randomer and the symbol "+T" means with randomer.
Figure 8B:
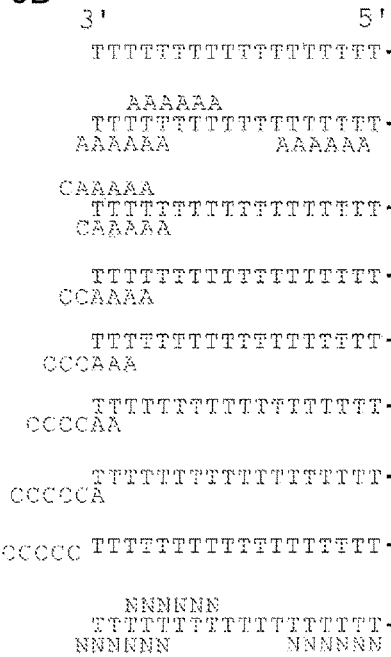
FIG. 8b shows possible hybridization of different hexamers in solution to a solid-phase poly-T sequence.
Figure 8C:
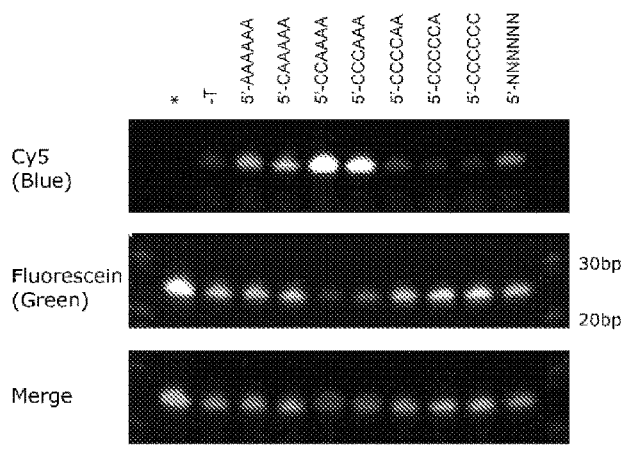
FIG. 8c shows denaturing PAGE analysis of a poly-T sequence extended with Duplase-3 and hexamers shown in FIG. 8b.
Figure 8D:
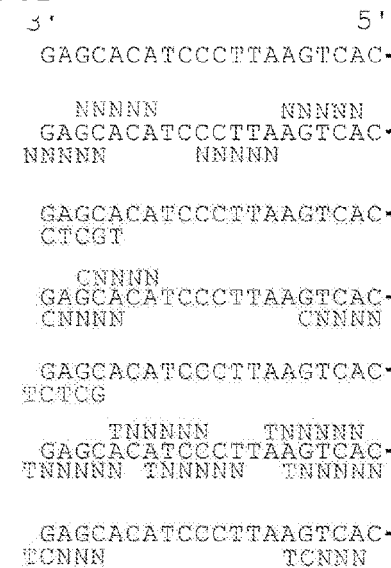
FIG. 8d shows possible hybridization of different pentamers in solution to a solid-phase oligo sequence (CACT-GAATTCCCTACACGAG (SEQ ID NO: 3)).
Figure 8E:
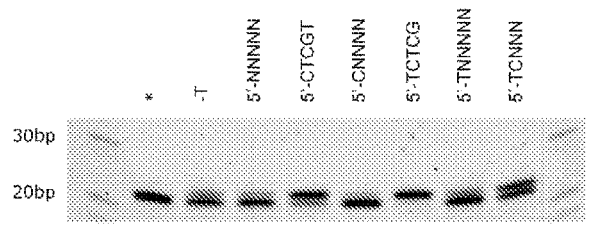
FIG. 8e shows denaturing PAGE analysis of the solid-phase oligo in FIG. 8d extended with the pentamers in 8d in the presence of the Duplase-3 and pentamers shown in FIG. 8d.

FIG. 7 shows that extension of single-stranded oligos can be achieved at various temperatures, including at about 60° C. Extension reaction temperature may have effects on the single-stranded extension with Duplase-3. Denaturing PAGE analysis of a 59-base solid-phase oligo extended with Duplase-3 and dCTP may show different effects at different reaction temperatures. FIG. 7a shows the results of reactions executed in the absence of a template in solution at temperatures of about 40° C., about 50° C., about 60° C., about 70° C., about 80° C., about 90° C., or about 100° C. FIG. 7b shows the results of reactions executed in the presence of 3'-phosphate blocked random hexamer templates in solution at temperatures of about 40° C., about 50° C., about 60° C., about 70° C., about 80° C., about 90° C., or about 100° C.

The single-stranded oligos can be extended at temperatures as high as about 40° C., about 50° C., about 60° C., about 70° C., about 80° C., about 90° C., or about 100° C., at which temperatures they may be capable of hybridizing two bases, three bases, four bases, five bases, or six bases. The single-stranded oligos can be extended at temperatures between 20° C. and 80° C., inclusive. In some cases, the temperature for the extension may be adjusted due to the considerations, including, for example, the stability of the oligonucleotide, the hybridization of the double-stranded complex, the stability of the immobilized or attached oligonucleotide on the support, etc.

Using Template in Solution

Extension of a surface-bound oligo can be enhanced by the addition of in-solution templates. These in-solution templates may be 3'-modified to prevent their elongation by the polymerase in competing reactions against the primers. For example, random hexamer priming can be used in the present single stranded nucleic acid extension reactions. As used herein, a randomer consists of bases whose sequence is random. All combinations of four bases at each N position would exist in the reaction mixture. For example, a random hexamer consists of six bases whose sequence is random at all six positions.

As shown in FIG. 8, random hexamers may increase incorporation of both templated and non-templated bases in reactions with Duplase-3 and a solid-phase bound primer. FIG. 8a shows the extension of a solid-phase bound oligo with the addition of randomers to the reaction solution. As used herein, a randomer is a nucleic acid whose sequence is random. The denaturing PAGE analysis may show the results of a 20-base oligo extended with Duplase-3 and 3'-O-azidomethyl-dNTPs without added template to solution (−T) or with the addition of 3'-phosphate blocked random hexamers to the reaction solution (+T). The sign * indicates unreacted control. FIG. 8b shows possible hybridization pairings of different templates in solution to a solid-phase bound poly-T sequence. Templates used may be hexamers. FIG. 8c shows an example that the polymerase requires at least three bases of hybridization with a template in solution for the primer extension to be successful. Denaturing PAGE analysis of a poly-T sequence extended with Duplase-3 and Cy5-ddGTP in the presence or absence of hexamers. Some 3'-phosphate blocked hexamers as shown in FIG. 8c may be used in reaction solutions with their sequences listed. The sign * indicates unreacted control. The sign −T indicates reactions without adding template. Reactions with templates that can hybridize three or more bases with the poly-T sequence may display better incorporation of the guanidine base in the presence of Duplase-3. After extension with Duplase-3, all samples were incubated with terminal deoxynucleotidyl transferase (TdT) and fluorescein-12-ddUTP to label any primer that has not been extended with Duplase-3. FIG. 8d shows possible hybridization pairings of different templates in solution to a solid-phase bound oligo (CACTGAATTCCCTACACGAG (SEQ ID NO: 3)). Templates used may be pentamers. Some potential sequence alignments during transient hybridization reactions may be illustrated as shown in FIG. 8d. FIG. 8e shows the extension results of the solid-phase oligo shown in FIG. 8d with specific, random, and semi-random templates in solution. Denaturing PAGE analysis may be shown for the sequence CACTGAATTCCCTACACGAG (SEQ ID NO: 3) after extension with Duplase-3 and 3'-O-azidomethyl-dCTP. Some 3'-phosphate blocked pentamers can be used in reaction solutions with their sequences listed. The sign * indicates unreacted control. The sign −T indicates reactions without added template.

Similar to extension reactions with single-stranded oligos, reactions with random templates in solution may be conducted at temperatures of about 40° C., about 50° C., about 60° C., or about 70° C. (FIG. 7b).

Figure 9:
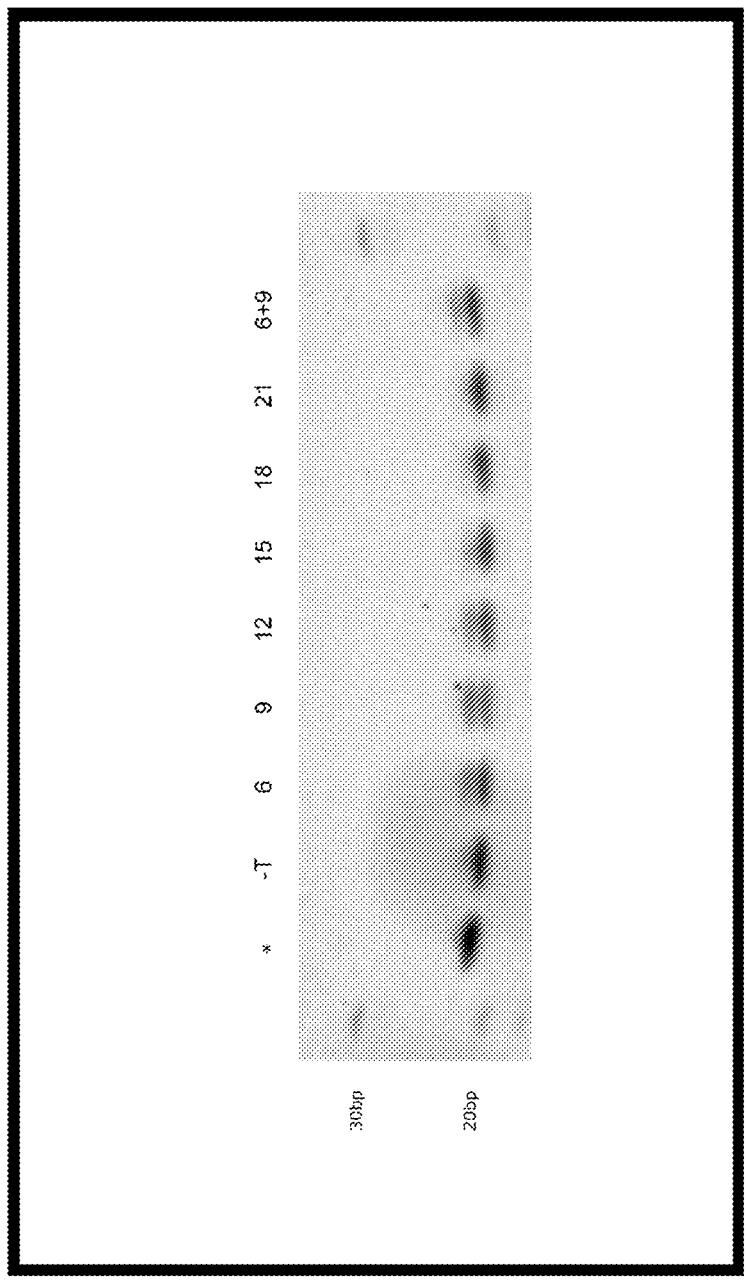
FIG. 9 shows an example of denaturing PAGE analysis of Duplase-3 to incorporate nucleotide on a 20-base single-stranded oligonucleotide in the presence of 3'-phosphate blocked randomers solution.

FIG. 9 shows the reaction yields for randomers with different lengths in solution (6, 9, 12, 15, 18, 21, or mixed 6+9 bases). The denaturing PAGE analysis shows the results of a 20-base solid-phase oligo extended with Duplase-3 and 3'-O-azidomethyl-dATP with 3'-phosphate blocked random templates in solution. The sign * indicates unextended control. The sign –T indicates control sample without in-solution template added.

Duplases may perform chain elongation of the growing strand when there are three consecutive nucleotides hybridizing to a target in solution and at least one 3' overhang base for efficient solid-phase primer extension opposite an oligo in solution (FIG. 8). Duplases may perform chain elongation of the growing strand when there are two, three, four, five, six, or seven consecutive nucleotides hybridizing to a target in solution and at least one 3' overhang base for efficient solid-phase primer extension opposite an oligo in solution. Theoretically 1024 possible sequence combinations may exist for a pentamer. Thus, it may be impractical to stock in-solution templates that can perfectly hybridize to and template any possible sequences. Four different possible sequence combinations exist for a semi-random sequence with a fixed 5' base, where X templates the incoming base and N is a random base (A, T, C, or G). Sixteen different possible sequence combinations exist for a semi-random sequence, XYNNN with two fixed 5' bases where X templates the incoming base and Y is complementary to the last base of the solid-phase oligo. For example, AGNNN should template the incorporation of thymine when the 3' base of the solid-phase primer is cytosine. Semi-random sequences increase the yield of extended primers (FIG. 8). Examples of semi-random sequences may include, for example, NXYNN or NNXTN.

Universal Templating Oligos

Universal templating oligos (UTOs) may be developed to template any base to make the enzymatic synthesis of any sequence possible by cyclic reversible termination. For example, they may be designed as UTO-1 described herein or as universal bases, such as one or more 5-nitroindole or 7-nitroindole bases. One such universal base may include 5-nitro-1-indolyl-3'-deoxyribose (5-NI). However, there may not be a universal base that meets all of the desired requirements; ability to pair with all natural bases equally, prime DNA synthesis by DNA polymerases, and direct incorporation off each of the natural nucleotides. DNA polymerases may not incorporate nucleotides well at positions opposite to or past most universal bases due to the lack of hydrogen bonding with many of them. Further, even if polymerases may overcome this barrier and incorporate opposite a universal base, the polymerase may not continue the DNA synthesis past a position lacking hydrogen bonding. Duplase extension of a poly-T sequence may not be improved by consecutive internal 5-NI bases.

The universal templating oligo UTO-1 (shown in FIG. 10) may contain all codons and includes poly-T sequences at the 3' and 5' ends that serve as spacers. The 3' deoxyuracil can be enzymatically cleaved using a combination of Uracil-DNA Glycosylase and apurinic/apyrimidic endonuclease to isolate any enzymatically synthesized fragments. All ANN, TNN, CNN, and GNN sequences may be contained within UTO-1, meaning that any combination of 2-base at the 3' end of the primer can be templated during repetitive synthesis steps to incorporate any of the A, T, C and G bases. For example, 20-base sequence enzymatically synthesized oligo-1 (ESO-1) may be synthesized based on template UTO-1 using Duplase-3. FIG. 10 also shows examples of oligo sequences used for extension reactions, sequencing library preparation, and sequencing analysis discussed in the present application. Modifications (e.g., 5'-biotinylation, 3'-deoxyuracil, 3'-phosphates, and thio bonds) may be listed in FIG. 10 according to ordering specifications for IDT.

Other ways to cleave the UTO after the synthesis of the growing strand are possible. In some cases, the UTO cleaving cleaves away the enzymatically synthesized oligonucleotide. In some cases, the UTO cleaving cleaves within the enzymatically synthesized fragment of the growing strand/hybridizing complex and consequently removes the UTO. In some cases, the UTO cleaving cleaves within the UTO. In some embodiments, the cleaving cleaves at the 3'-end of UTO. In some embodiments, the UTO cleaving cleaves at the 5'-end of UTO. In some cases, the UTO cleaving uses photo chemistry to cleave the UTO. In some cases, the UTO cleaving uses acidic or basic conditions to cleave the UTO.

Enzymatic Oligonucleotide Synthesis Methods

Reversible terminators may be enzymatically purified using a polymerase that can incorporate dNTPs but not 3'-O-azidomethyl dNTPs such as Taq or Klenow. Neutralization following cleavage of the reversible terminators may also prevent second base synthesis.

When using 3'-O-azidomethyl reversible terminators, TCEP can be instantly neutralized with, for example, iodoacetamide.

Figures 11A, 11B:
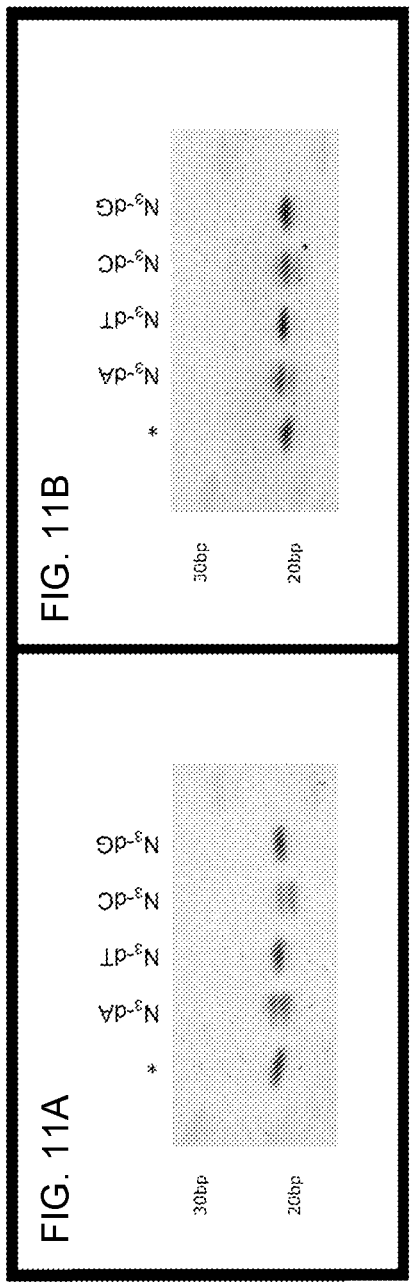
FIG. 11a shows an example of denaturing PAGE analysis following extension of a 20-base oligonucleotide by Duplase-3.
FIG. 11b shows another example of denaturing PAGE analysis following extension of a 20-base oligonucleotide by Duplase-3.

The step-wise efficiency may be improved by using a more concentrated stock of the polymerases or other enzymes (FIG. 11). Denaturing PAGE analysis shows the results following an extension of a 20-base oligo by Duplase-3 using 3'-O-azidomethyl reversible terminators in a reaction containing 1 μg Duplase-3, 200 mM NaCl, and 20 mM Tris-HCl at pH 8.0 (shown in FIG. 11*a*), or 2 μg Duplase-3, 80 mM NaCl, and 8 mM Tris-HCl at pH 8.0 (shown in FIG. 11*b*). The sign * indicates unextended primer control. These new reaction conditions may result in an increase of incorporation of non-templated bases on a single-stranded oligo.

Oligo synthesis yields can be enhanced by the addition of a capping step after the addition of each reversible terminator but before the cleavage step for the terminator. One method to achieve this may be conducting the extension using a dideoxy nucleotide and TdT and/or Duplase. Under the above conditions, oligos that are not extended with a reversible terminator may be truncated and may not be able to be extended in subsequent steps.

If the final base added during synthesis is modified to select for only full-length sequences or if a 3' OH is required for subsequent utilization, this capping step may provide a simple method of purification. For example, one may modify the 3' end with a biotinylated base in the final synthesis step; then full-length oligos could be captured on a streptavidin-coated surface and truncated oligos may be left behind. Another purification method may involve synthesis using a nucleotide with a 3'-group that cannot be recognized by 3' exonucleases, thus allowing the truncated oligos to be enzymatically removed.

In some cases, other modified sugars may be used in the growing strand synthesis as well. For example, xeno nucleic acid (XNA) is a synthetic alternative to the natural nucleic acids DNA and RNA as information-storing biopolymers that differs in the sugar backbone. XNA type of research may include the types of synthetic XNA, such as, for example, 1,5-anhydrohexitol nucleic acid (HNA), cyclohexene nucleic acid (CeNA), threose nucleic acid (TNA), glycol nucleic acid (GNA), locked nucleic acid (LNA), and peptide nucleic acid (PNA). Fluorescence-labeled nucleotides and other non-natural nucleotides are other possible substrates for the enzyme to extend the growing strand.

Polymerase engineering may lead to faster, more efficient synthesis. Lower-fidelity polymerases that misincorporate at a high rate may not require the base in solution to be templated. UTO may be shortened further so that its only function is to promote hybridization at the 3' terminus. Reaction times may decrease as well if the 3' terminus is hybridized but the base in solution is not templated but still added by a low-fidelity polymerase.

Materials and Methods

Primer Extension Assays on Double-Stranded DNA

Primers were hybridized to a biotinylated target sequence immobilized on streptavidin-coated magnetic beads (Dynabeads MyOne Streptavidin T1, Thermo Fisher, Waltham, Mass.) by heating to 70° C. for five minutes then 55° C. for 15 minutes then 25° C. for five minutes in RB buffer (1 M sodium chloride, 2 5 mM Tris-HCl pH 7.5, 0.01% TWEEN20). 0.1 mg of beads were used per 25 µL reaction volume. Reactions were started by the addition of nucleotide at selected temperature and stopped by the addition of a 1.6× volume of RB buffer. The hybridized primer was stripped from the bead-bound template using 0.1 N sodium hydroxide for ten minutes at room temperature and analyzed by denaturing PAGE. All oligos were purchased from Integrated DNA Technologies (IDT, Redwood City, Calif.). Sequences are listed in FIG. 10.

Preparation of Single-Stranded DNA on a Solid Surface for Extension

Single-stranded oligos were immobilized to streptavidin coated beads. 0.1 mg of beads were used per 25 µL reaction volume. Reactions were started by the addition of nucleotide at selected temperature and stopped by the addition of a 1.6× volume of RB buffer. The immobilized primer was stripped from the bead-bound template in 0.1 N sodium hydroxide for five minutes at 65° C. and analyzed by denaturing PAGE. Oligos were purchased from IDT and are listed in FIG. 10.

Primer Extension Reactions with Duplase Enzymes

For reactions on double-stranded DNA, magnetic beads were prepared as previously described with immobilized template and hybridized primer. Beads were washed in reaction buffer and then resuspended in the reaction mix containing a final concentration of 20 mM Tris-HCl at pH8.8, 10 mM ammonium sulfate, 10 mM KCl, 0.1% Triton X-100, 2 mM $MgSO_4$, 1 mg/mL bovine serum albumin (Sigma-Aldrich, St. Louis, Mo.), 4 µg/mL polyvinylpyrrolidone 10, and 1 µg of enzyme. Reaction mixtures were pre-warmed to 45° C., and nucleotide was added to a final concentration of 2 µM. Reactions were allowed to proceed for one minute before stopping for analysis by denaturing PAGE. Extension reactions on single-stranded DNA were performed as previously described though buffer components, reaction times and temperatures, and nucleotide concentrations varied extensively across experiments conducted for research purposes. Optimized conditions for the synthesis of the 20-base ESO-1 sequence are described below.

Cleavage of Reversible Terminators

After incorporation of reversible terminators, beads were resuspended in 50 mM TCEP at pH9.0 (Gold Bio, Olivette, Mo.) and incubated at 60° C. for 10 minutes. The TCEP solution was removed, and beads were resuspended in RB buffer and transferred to a new reaction vessel.

Synthesis of 20-Base ESO-1 Sequence with UTO-1

Beads were prepared as previously described with immobilized UTO-1. 0.2 mg of beads were used in 50 µL reactions containing 200 mM NaCl, 20 mM Tris at pH 8.0, 8 mM $MnCl_2$, 1 µg Duplase-3, and 100 µM of a 3'-O-azidomethyl-dNTP. Reactions were allowed to proceed for one hour before stopping. The sequence ESO-1 was synthesized by the incorporation of 3'-O-azidomethyl-dCTP followed by cleavage with TCEP and the incorporation of 3'-O-azidomethyl-dGTP, followed by cleavage with TCEP, etc. For the first synthesis, after the addition of 4, 8, 12, 16, and 20 bases, 0.025 mg of beads was removed from solution, and the oligo was stripped from beads and analyzed by denaturing PAGE. Volumes for next steps were adjusted accordingly. After the final incorporation/cleavage step, the oligo with ESO-1 sequence was used for sequencing.

Extension Reactions with MMLV Reverse Transcriptases

Two MMLV reverse transcriptases, Superscript IV (Thermo Fisher) and SMARTScribe (Clonetech, Mountain View, Calif.), were tested for their ability to incorporate nucleotides on both double-stranded and single-stranded oligos. Both enzymes were desalted using Zeba Spin Desalting Columns (Thermo Fisher) to remove 2-mercaptoethanol from the enzyme storage buffer. Protein was quantified before and after desalting using Qubit (Thermo Fisher) and analyzed by SDS-PAGE. For reactions on double-stranded DNA, magnetic beads prepared as previously described with immobilized template and hybridized primer were washed in reaction buffer and then resuspended in the reaction mix containing a final concentration of 20 mM Tris-HCl at pH 8.8, 10 mM ammonium sulfate, 10 mM KCl, 0.1% Triton X-100, 4 mM $MnCl_2$, and 3 µL of desalted enzyme. Reaction mixtures were pre-warmed to 50° C. for Superscript IV or 42° C. for SMARTScribe and nucleotides were added to a final concentration of 10 µM. Reactions were allowed to proceed for two hours. For reactions on single-stranded DNA, magnetic beads prepared as previously described and immobilized with a single-stranded oligo were washed in reaction buffer and then resuspended in 22 µL reaction mix containing a final concentration of 20 mM Tris-HCl pH 8.8, 10 mM ammonium sulfate, 10 mM KCl, 0.1% Triton X-100, 4 mM $MnCl_2$, and 10 µM nucleotide. Reaction mixtures were pre-warmed to 50° C. for Superscript IV and started by addition of 3 µL desalted enzyme. For SMARTScribe, reaction mixtures were heated to 72° C. and snap-cooled on ice. Samples were then incubated at 42° C. and reactions were started with the addition of 3 µL desalted enzyme. Reactions were allowed to proceed for two hours.

Fluorescent Labeling of Oligos with Terminal Deoxynucleotidyl Transferase (TdT)

Labeling of poly-T sequences, which do not stain well with SYBR Gold, was accomplished by end-labeling oligos with TdT (New England Biolabs, Ipswich, Mass.) and fluorescein-12-ddUTP (Perkin Elmer, San Jose, Calif.) by incubating 0.1 mg of beads with 5 µM nucleotide and 20 U of enzyme in 20 mM Tris-HCl pH 7.5, 10 mM ammonium sulfate, 10 mM KCl, 0.1% Triton X-100, and 0.5 mM $MnCl_2$. Reactions were allowed to proceed for 3 hours at 37° C. before heat-inactivation of the enzyme for 20 minutes at 75° C.

Sequencing of SPO-13 with Synthesized 20 Base ESO-1 Sequence

The SPO-13-ESO-1 oligo still on beads was poly adenylated using TdT (Roche, Santa Clara, Calif.) and Duplase-1. Illumina adapters were added to these sequences using PCR, a poly(T)-tailed P7 adapter sequence, P7-Poly (T), and an oligo with the sequence PCR-ESO1-FPCR was repeated with Illumina P5 and P7 adapter oligos, and the library quality was analyzed by bioanalyzer and qPCR. All oligos were purchased from IDT. A MiSeq nano flow cell (Illumina) was clustered with a 4 pM library comprised of 90% PhiX and 10% PCR-prepared library. 150 step paired end cycling was run using a V2 kit (Illumina), and the ESO-1 sequence was identified by manually sorting first output reads.

Denaturing PAGE

Samples were resolved by electrophoresis in 6% or 15% polyacrylamide TBE-Urea gels (Thermo Fisher) in TBE. Gels were stained in SYBR Gold (Thermo Fisher) for five to ten minutes at room temperature and imaged on a Bio-Rad ChemiDoc MP system. Fluorescent products were visualized before and after staining.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of synthesizing a single-stranded oligonucleotide, comprising:
   (a) providing a single-stranded primer comprising a free 3' end and a 5' end immobilized on a solid surface, a polymerase, and a nucleotide reagent, wherein said nucleotide reagent is a reversible terminator nucleotide bearing a 3' terminator, and said polymerase is a duplase;
   (b) hybridizing a hybridization site on said single-stranded primer with a complementary fragment on a template, wherein said hybridization site is at said 3' end and comprises no more than 7 bases;
   (c) extending said single-stranded primer from said free 3' end with said nucleotide reagent by said polymerase; and
   (d) separating said hybridization site and said complementary fragment, thereby forming an extended single-stranded primer immobilized on said solid surface;
   wherein said polymerase requires no more than 7 base pairings to extend said single-stranded primer.

2. The method of claim 1, wherein said polymerase is a modified duplase.

3. The method of claim 1, further comprising:
   e) removing said 3' terminator from said reversible terminator nucleotide.

4. The method of claim 3, further comprising:
   (f) repeating steps (a)-(e).

5. The method of claim 1, wherein said template is said single-stranded primer, or an adjacent single-stranded nucleic acid immobilized on said solid surface.

6. The method of claim 5, wherein said template is said adjacent single-stranded nucleic acid, and wherein said adjacent single-stranded nucleic acid shares no more than 5%, no more than 10%, no more than 15%, no more than 20%, no more than 25%, no more than 30%, no more than 35%, no more than 40%, no more than 45%, no more than 50%, no more than 55%, no more than 60%, no more than 65%, no more than 70%, no more than 75%, no more than 80%, no more than 85%, no more than 90%, or no more than 95% sequence identity with said single-stranded primer.

7. The method of claim 5, wherein said template is said adjacent single-stranded nucleic acid, and wherein said adjacent single-stranded nucleic acid shares 100% sequence identity with said single-stranded primer.

8. The method of claim 1, wherein said hybridization site is 1, 2, 3, 4, 5, 6 or 7 bases in length.

9. The method of claim 4, wherein said repeating in (f) extends said single-stranded primer from said 3' free end, thereby synthesizing a single-stranded oligonucleotide product comprising said single-stranded primer.

10. A method of synthesizing a single-stranded oligonucleotide, comprising:
    (a) providing a solid surface comprising a plurality of single-stranded primers immobilized on said solid surface via 5' ends of said plurality of single-stranded primers, a polymerase, and a first reversible terminator nucleotide, wherein said polymerase is a duplase;
    (b) forming a duplex having 1 to 7 base-pairs in length, wherein said duplex comprises a 3' end of a first primer of said plurality of single-stranded primers; and
    (c) attaching said first reversible terminator nucleotide at said 3' end of said first primer, thereby forming a first 3'-blocked extended primer;
    wherein said duplex further comprises a complementary oligonucleotide with regard to said 3' end of said first primer, and wherein said complementary oligonucleotide is immobilized on said solid surface.

11. The method of claim 10, wherein said complementary oligonucleotide is part of said first primer or another primer of said plurality of single-stranded primers.

12. The method of claim 10, further comprising:
    (d) separating said duplex and removing a 3' terminator on said first reversible terminator nucleotide of said first 3'-blocked extended primer, thereby forming a first extended primer comprising a free 3' end and completing a first cycle.

13. The method of claim 12, further comprising:
    (e) adding a second reversible terminator nucleotide;
    (f) forming another duplex having 1 to 7 base-pairs in length, wherein said another duplex comprises a 3' end of said first extended primer;
    (g) attaching said second reversible terminator nucleotide at said free 3' end of said first extended primer, thereby forming a second 3'-blocked extended primer; and
    (h) separating said another duplex and removing another 3' terminator on said second reversible terminator nucleotide of said first 3'-blocked extended primer, thereby forming a second extended primer comprising another free 3' end and completing a second cycle;

wherein said another duplex further comprises another complementary oligonucleotide, and wherein said another complementary oligonucleotide is immobilized on said solid surface.

14. The method of claim 12, further comprising: repeating (a)-(d) in additional cycles and adding an additional reversible terminator nucleotide in each of said additional cycles; thereby synthesizing a single-stranded oligonucleotide product comprising said first primer and an additional sequence extended from said 3' end of said first primer, wherein said repeating and said attaching are conducted in the absence of a solution-based oligonucleotide template comprising a sequence complementary to said additional sequence.

* * * * *